(12) United States Patent
Sato

(10) Patent No.: US 10,391,000 B2
(45) Date of Patent: Aug. 27, 2019

(54) TRANSPORT DEVICE AND DISPOSABLE WEARABLE ARTICLE PRODUCTION METHOD USING SAME

(71) Applicant: ZUIKO CORPORATION, Osaka (JP)

(72) Inventor: Hitoshi Sato, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 154 days.

(21) Appl. No.: 15/575,958

(22) PCT Filed: May 6, 2016

(86) PCT No.: PCT/JP2016/063638
§ 371 (c)(1),
(2) Date: Nov. 21, 2017

(87) PCT Pub. No.: WO2016/190065
PCT Pub. Date: Dec. 1, 2016

(65) Prior Publication Data
US 2018/0153747 A1    Jun. 7, 2018

(30) Foreign Application Priority Data
May 28, 2015 (JP) .................................. 2015-108562

(51) Int. Cl.
*A61F 13/15* (2006.01)
*B29C 65/00* (2006.01)
*B29L 31/48* (2006.01)

(52) U.S. Cl.
CPC .... *A61F 13/15764* (2013.01); *A61F 13/1565* (2013.01); *A61F 13/15723* (2013.01);
(Continued)

(58) Field of Classification Search
CPC ............. B29C 66/0326; B29C 66/0324; A61F 13/15804; A61F 13/15747;
(Continued)

(56) References Cited

U.S. PATENT DOCUMENTS 8,327,904 B2 * 12/2012 Yamamoto ........ A61F 13/15723
156/199
2002/0125105 A1 * 9/2002 Nakakado ......... A61F 13/15764
198/471.1
(Continued)

FOREIGN PATENT DOCUMENTS

| JP | 2010-63716 | 3/2010 |
|---|---|---|
| JP | 2010-115427 | 5/2010 |
| WO | 01/44086 | 6/2001 |

OTHER PUBLICATIONS

Extended European Search Report dated Feb. 23, 2018 in European Application No. 16799773.3.
(Continued)

*Primary Examiner* — Vishal I Patel
(74) *Attorney, Agent, or Firm* — Wenderoth, Lind & Ponack, L.L.P.

(57) ABSTRACT

A holding region includes opposite skirt portions in a revolution direction of a holding pad each of which has at least opposite ends in a specific direction that extend along a first curve when the holding pad is at a first revolution position. The holding region includes a second area bearing on at least part of one side portion and at least part of the other side portion in a revolution direction of the holding pad when the holding pad is at a second revolution position that extends along a second curve. A delivery side holding region includes opposite side portions in the specific direction each of which has at least opposite ends in a rotational direction, each end being formed with a first recess. The first recess having a bottom surface that extends along an arc of the first curve.

13 Claims, 15 Drawing Sheets

(52) U.S. Cl.
CPC .. *A61F 13/15747* (2013.01); *A61F 13/15804* (2013.01); *B29C 66/0324* (2013.01); *B29C 66/0326* (2013.01); *B29L 2031/4878* (2013.01)

(58) Field of Classification Search
CPC ............ A61F 13/15723; A61F 13/1565; A61F 13/15764; B29L 2031/4878
See application file for complete search history.

(56) References Cited

U.S. PATENT DOCUMENTS

2010/0122766 A1  5/2010  Yamamoto
2013/0140755 A1  6/2013  Ninomiya et al.

OTHER PUBLICATIONS

International Search Report dated Jul. 19, 2016 in International (PCT) Application No. PCT/JP2016/063638.

* cited by examiner

TRANSPORT DEVICE AND DISPOSABLE WEARABLE ARTICLE PRODUCTION METHOD USING SAME

TECHNICAL FIELD

The present invention relates to a device for transporting an object onto a sheet.

BACKGROUND ART

In a conventional process of producing wearable articles such as disposable diapers that include an absorber capable of absorbing liquid, the absorber, i.e. an object of transportation, is transported and joined onto a surface of a sheet constituting a waist section of the wearable article.

A device disclosed in Patent Literature 1 is known as an example of the device for transporting the absorber to the sheet surface, for example.

Specifically, the device disclosed in Patent Literature 1 includes a first roller for holding an absorber on a circumferential surface thereof, a second roller (roller mechanism) for guiding a sheet (third web) in a horizontal direction, and a third roller (rotary drum) for receiving the absorber from the first roller at a predetermined receiving position, the first roller being in the form of a cylinder rotatable about a predetermined axis, and delivering the absorber to the sheet being guided by the second roller at a predetermined delivery position. The third roller includes a holding pad (suction pad) for holding the absorber, and a turning mechanism for turning the holding pad through 90 degrees in the course of movement from the receiving position to the delivery position. The holding pad has an outer surface having such a shape that the central portion thereof bulges radially outward of the third roller.

In the device disclosed in Patent Literature 1, the central portion of the outer surface of the holding pad of the third roller bulges radially outward of the third roller, i.e. toward the first roller, whereas the circumferential surface of the first roller is simply in the form of a cylindrical surface. Therefore, there is a problem that the absorber held on the circumferential surface of the first roller could not be brought into close contact with the circumferential surface of the second roller, and thus the object such as the absorber could not be appropriately transported.

CITATION LIST

Patent Literature

Patent Literature 1: Japanese Unexamined Patent Publication No. 2010-115427

SUMMARY OF INVENTION

The present invention aims to provide a transport device capable of transporting an object more appropriately and a method for producing a disposable wearable article using the transport device.

In order to achieve the above-mentioned aim, the present invention provides a transport device for transporting an object to a surface of a sheet, comprising: a delivery roller rotatable about a first rotational axis extending in a specific direction for transporting the object while holding the object on a circumferential surface thereof; and an intermediate transporter including a main section rotatable about a second rotational axis extending in parallel to the first rotational axis, and a holding pad mounted on the main section in such a way as to revolve about the second rotational axis according to the rotation of the main section, the holding pad receiving the object onto an outer surface of the holding pad from the circumferential surface of the delivery roller at a first revolution position where the holding pad faces the delivery roller, and delivering the object onto the sheet from the outer surface of the holding pad at a second revolution position, wherein: the outer surface of the holding pad includes a holding region for holding the object; the intermediate transporter includes a turning mechanism for turning the holding pad about a turning axis perpendicularly intersecting the second rotational axis in the course of the movement of the holding pad from the first revolution position to the second revolution position; the holding region includes opposite skirt portions in a revolution direction of the holding pad each of which has at least opposite ends in the specific direction that extend along a first curve when the holding pad is at the first revolution position; the holding region includes a second area bearing on at least part of one side portion and at least part of the other side portion in the revolution direction of the holding pad, the second area extending along a second curve, when the holding pad is at the second revolution position; the first curve is on an arc of a circle centered on the second rotational axis in a view along the second rotational axis when the holding pad is at the first revolution position; the second curve is on an arc of a circle centered on the second rotational axis in a view along the second rotational axis when the holding pad is at the second revolution position; the circumferential surface of the delivery roller includes a delivery side holding region for holding the object; the delivery side holding region includes opposite side portions in the specific direction, each of the side portions having at least opposite ends in a rotational direction of the delivery roller, each end being formed with a first recess extending radially inward of the delivery roller, the first recess having a bottom surface whose intersecting line of a plane passing through the first rotational axis and the second rotational axis extends along the arc of the first curve in a view along the revolution direction of the holding pad, when the delivery side holding region and the holding region of the holding pad face each other.

Further, the present invention provides a method for producing a disposable wearable article using the transport device configured in the above-mentioned manner, the wearable article including a waist section to be placed around the waist of a wearer and a crotch section to be placed on the crotch of the wearer, the method comprising: a waist sheet transport step of transporting a sheet for forming the waist section in a longitudinal direction thereof; an absorber joining step of transporting an absorber to be placed on a portion corresponding to the crotch section using the transport device and joining the absorber to the sheet to form a joined assembly; a double folding step of folding the joined assembly in half in a direction perpendicularly intersecting the longitudinal direction; a side seal formation step of forming side seals by joining overlapping portions of the sheet that lie on both sides of the absorber in the longitudinal direction; and a cutting step of cutting the sheet in such a way that the side seals remain on the portions on the both sides of the absorber in the longitudinal direction to form a disposable wearable article.

According to the present invention, it is possible to transport an object more appropriately.

DESCRIPTION OF EMBODIMENTS

Hereinafter, an embodiment of the present invention will be described with reference to the accompanying drawings. Here, a case will be described in which an object of transportation is an absorber for use in a disposable diaper (wearable article). It should be noted that the following embodiment illustrates an example of the invention, and does not delimit the protection scope of the invention.

(1) Structure of Disposable Diaper

Figure 1:
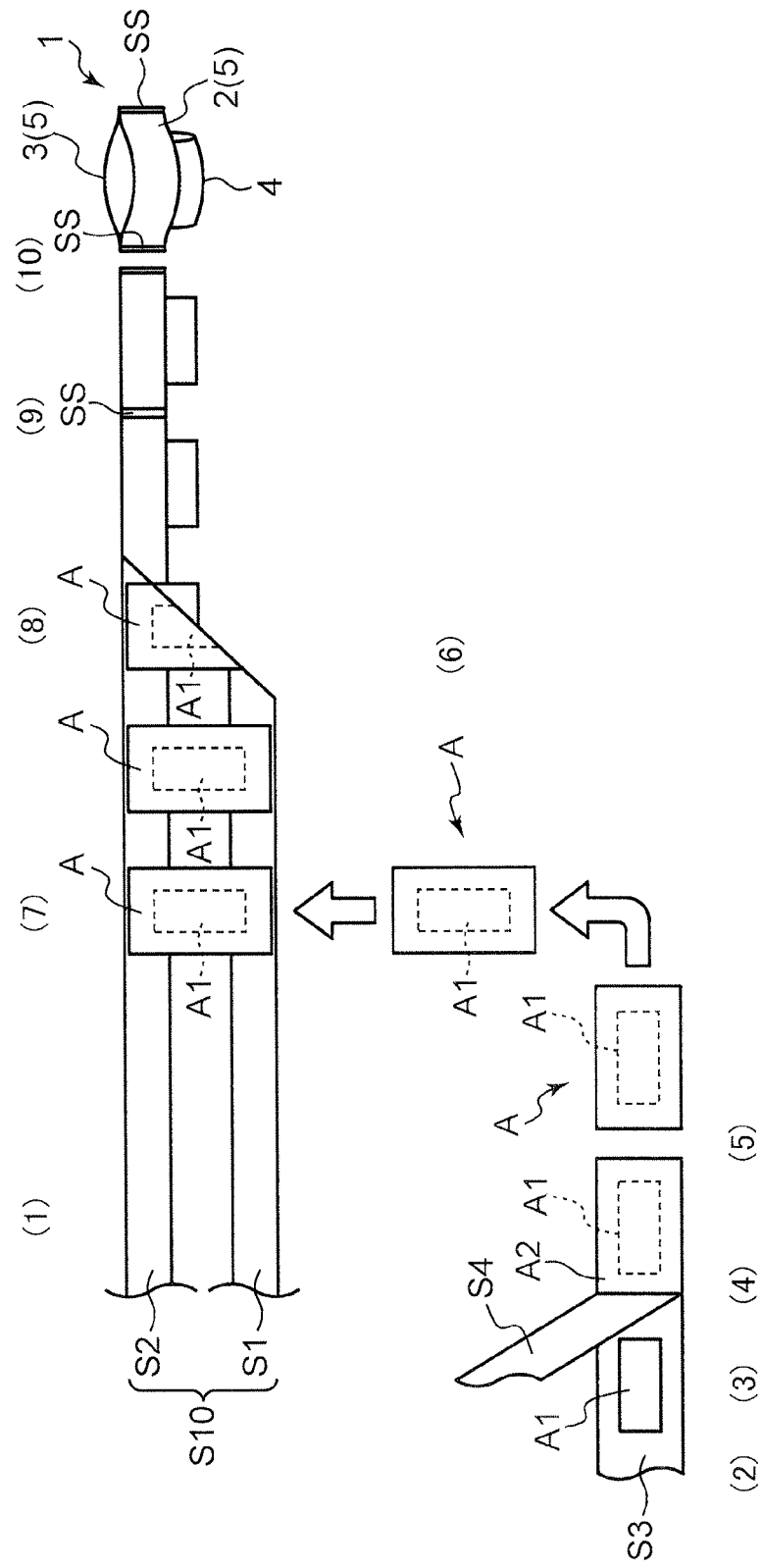
FIG. 1 is a schematic process diagram showing a method for producing a disposable wearable article according to the present invention.

FIG. 1 is a process diagram showing a method for producing a disposable diaper 1 illustrated as an example of a disposable wearable article according to the present invention.

The disposable diaper 1 includes a waist section 5 having a front abdominal portion 2 to be placed on the front abdomen of a wearer and a rear dorsal portion 3 to be placed on the buttocks of the wearer, and a crotch section 4 to be placed on the crotch of the wearer.

An end of the front abdominal portion 2 and an end of the rear dorsal portion 3 are joined together by a side seal SS. Each of the front abdominal portion 2 and the rear dorsal portion 3 is stretchable. Specifically, the front abdominal portion 2 and the rear dorsal portion 3 can each be formed by using an elastic material (elastic nonwoven fabric) for itself or by placing an elastic member between a pair of sheets made of nonwoven fabric in a stretched state. The elastic member can be formed of polyurethane, natural rubber, or thermoplastic resin. Further, the elastic member can be formed in a thread shape or ribbon shape.

The crotch section 4 is joined to the front abdominal portion 2 and the rear dorsal portion 3 in such a way as to extend over the front abdominal portion 2 and the rear dorsal portion 3. The crotch section 4 has an approximately rectangular planar shape, and has opposite ends in a longitudinal direction thereof that are respectively joined to the front abdominal portion 2 and the rear dorsal portion 3.

The crotch section 4 according to the present embodiment is constituted by an absorber A capable of absorbing body fluid such as urine of the wearer. In the present embodiment, an elastic member is attached to opposite ridges of the absorber A in a width direction (a direction perpendicularly intersecting the longitudinal direction) thereof in a state of being stretched in the longitudinal direction of the absorber A. The absorber A contracts in such a way as to bring the front abdominal portion 2 and the rear dorsal portion 3 closer to each other in a state of being joined to the front abdominal portion 2 and the rear dorsal portion 3.

The absorber A includes a liquid permeable top sheet S4, a cover sheet S3, and an absorbent core A1 disposed between these sheets S3 and S4.

The top sheet S4 is disposed on the skin of the wearer. The cover sheet S3 is disposed on the opposite side with respect to the skin of the wearer. The top sheet S4 can be formed of nonwoven fabric or a mesh sheet that permits permeation of liquid therethrough. The cover sheet S3 can be formed of a polyethylene film having air permeability, nonwoven fabric having water repellency and air permeability, or a sheet obtained by laminating these materials.

The absorbent core A1 is provided for absorbing body liquid having entered therein through the top sheet S4. The absorbent core A1 has a greater thickness than the top sheet S4 and the cover sheet S3. In the present embodiment, the absorbent core A1 has an approximately rectangular planar shape. The absorbent core A1 is disposed on a central portion (a portion of the absorber A excluding its peripheral edge) such that a longitudinal direction thereof agrees with the longitudinal direction of the absorber A.

The absorbent core A1 can be formed by laminating fluff layers, the fluff being obtained by grinding a roll pulp for defibration. It is possible to mix superabsorbent polymer particles in the fluff. Alternatively, the absorbent core A1 may be formed only of nonwoven fabric or nonwoven fabric carrying superabsorbent polymer particles without using fluff.

It should be noted that although in the present embodiment, the front abdominal portion 2 and the rear dorsal portion 3 are constituted by separate members, the front abdominal portion 2 and the rear dorsal portion 3 are not limited to this structure. For example, it is possible to use a sheet including a portion corresponding to the front abdominal portion 2, a portion corresponding to the rear dorsal portion 3, two leg holes, and a portion between the leg holes for use as the crotch section 4. In this case, it is possible to join an absorber A onto the portion between the leg holes of the sheet.

(2) Method For Producing Disposable Diaper

Now, a method for producing the disposable diaper 1 configured in the above-mentioned manner will be described with reference to FIG. 1.

The production method of the disposable diaper 1 includes a waist sheet transport step (1), a crotch sheet transport step (2), a core joining step (3), a sheet joining step (4), an absorber joining step, a double folding step (8), a side seal formation step (9), and a cutting step (10). The absorber joining step includes an absorber cutting step (5), an absorber transport step (6) and a joining step (7).

In the waist sheet transport step (1), a sheet S10 for forming the waist section 5 is transported along a longitudinal direction thereof. In the present embodiment, the waist section 5 is constituted by the front abdominal portion 2 and the rear dorsal portion 3 as mentioned above. Therefore, in the waist sheet transport step (1), a front sheet S1 for forming the front abdominal portion 2 and a rear sheet S2 for forming the rear dorsal portion 3 are transported in respective longitudinal directions. The front sheet S1 and the rear sheet S2 are transported in parallel to each other. The waist sheet transport step (1) is performed with the front sheet S1 and the rear sheet S2 being applied with a predetermined tension until the cutting step (10) described later is performed.

In the crotch sheet transport step (2), the cover sheet S3 is transported in a longitudinal direction thereof. The elastic member is attached to widthwise opposite ridges of the cover sheet S3 in a state of being stretched in the longitudinal direction of the cover sheet S3. The crotch sheet transport step (2) is performed with the cover sheet S3 being applied with a predetermined tension in the longitudinal direction thereof until the absorber cutting step (5) described later is performed.

In the core joining step (3), the absorbent core A1 is joined onto the cover sheet S3. The absorbent core A1 is joined onto the cover sheet S3 such that the longitudinal direction thereof agrees with the transport direction of the cover sheet S3. The absorbent core A1 is joined onto the cover sheet S3 at a predetermined distance from another absorbent core A1 in its transport direction.

In the sheet joining step (4), the top sheet S4 is disposed on the cover sheet S3 such that the absorbent core A1 is sandwiched between the cover sheet S3 and the top sheet S4, and the top sheet S4 is joined onto the cover sheet S3 to form a continuum A2 of absorbers A.

In the absorber cutting step (5), the cover sheet S3 and the top sheet S4 are cut at a position between adjacent absorbent cores A1 to thereby separate an absorber A from the continuum A2. In this manner, the absorber A is formed that extends in the transport direction of the cover sheet S3 and has a substantially rectangular shape.

In the absorber transport step (6), the absorber A is transported to a position at which the absorber A extends over the front sheet S1 and the rear sheet S2.

Here, in the present embodiment, the cover sheet S3 is transported in parallel to the front sheet S1 and the rear sheet S2, and thus the longitudinal direction of the absorber A extends in parallel to the transport directions of the front sheet S1 and the rear sheet S2. On the other hand, the lengthwise opposite ends of the absorber A (crotch section 4) are respectively joined to the front abdominal portion 2 (front sheet S1) and the rear dorsal portion 3 (rear sheet S2) as mentioned above. Accordingly, in the absorber transport step (6), the absorber A is turned 90 degrees.

In the joining step (7), one end of the absorber A in the longitudinal direction is joined to the front sheet S1 and the other end of the absorber A in the longitudinal direction is joined to the rear sheet S2 to form a joint assembly (not denoted by a reference sign).

In the double folding step (8), the joint assembly is folded in half in a width direction thereof that perpendicularly intersects the longitudinal direction of the sheets S1 and S2.

In the side seal formation step (9), overlapping portions of the sheets S1 and S2 are joined to form side seals SS respectively at opposite ends of a part of the sheets S1 and S2 in the longitudinal direction.

In the cutting step (10), the sheets S1 and S2 are cut such that the side seals SS remain at the opposite ends of the part of the sheets S1 and S2 in the longitudinal direction to thereby form the disposable diaper 1.

In the above-mentioned production method, the front sheet S1 and the rear sheet S2 are transported in parallel to each other, and the absorber A is joined onto the sheets S1 and S2 such that the absorber A extends over the sheets S1 and S2. However, the production method according to the present invention is not limited to the above-mentioned one.

For example, in the waist sheet transport step (1), it is possible to transport a waist sheet including portions respectively corresponding to the front abdominal portion 2 and the rear dorsal portion 3. In this case, it is possible to form a plurality of leg holes in the waist sheet to thereby form a portion corresponding to the crotch section 4 in every region between adjacent leg holes of the waist sheet. In this case, in the joining step (7), the absorber A is joined to each portion between adjacent leg holes of the waist sheet.

(3) Apparatus For Producing Disposable Diapers

Figure 2:
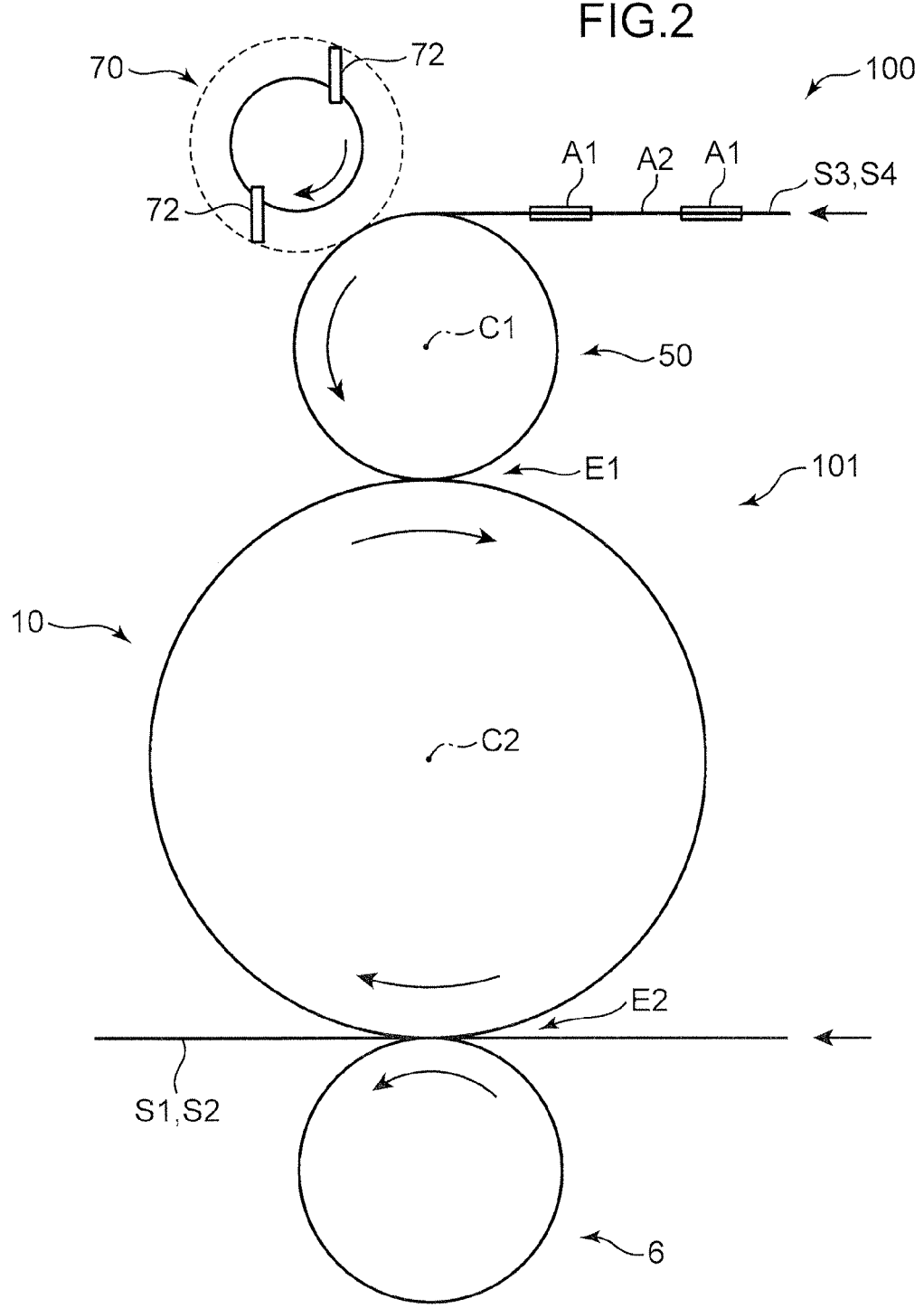
FIG. 2 is a schematic diagram showing a device for use in the production of the disposable wearable article shown in FIG. 1.

Now, a device to be used to perform the absorber cutting step (5), the absorber transport step (6) and the joining step (7) will be described with reference to FIG. 2. FIG. 2 is a schematic front view showing the device to be used to perform these steps included in a production apparatus 100 for producing disposable diapers.

(i) General Description of Apparatus

The production apparatus 100 includes a cutting roller 70, an anvil roller (delivery roller) 50, an intermediate transporter 10, and a sheet guide roller 6. Among these components, the anvil roller 50 and the intermediate transporter 10 function as a transport device 101 for transporting the absorber A to the sheets S1 and S2.

The sheet guide roller 6 is in the form of a rotary member rotatable about an axis extending in a specific direction (direction perpendicularly intersecting the drawing sheet surface of FIG. 2) for guiding the sheets S1 and S2. Hereinafter, the specific direction will be referred to as "front-rear direction".

When an unillustrated driving roller rotates, the sheets S1 and S2 are transported along a tangent line of the sheet guide roller 6. In the present embodiment, the sheets S1 and S2 are transported substantially horizontally while passing over an upper end of the sheet guide roller 6.

The cutting roller 70 is in the form of a rotary member rotatable around an axis extending in the front-rear direction, and includes cutting blades 72 on a circumference thereof. In the present embodiment, two cutting blades 72 are disposed on the circumferential surface of the cutting roller at a distance of 180 degrees from each other.

The anvil roller 50 is in the form of a rotary member rotatable around a first rotational axis C1 extending in the front-rear direction. The anvil roller 50 and the cutting roller 70 are connected to each other via a belt or the like, and synchronously rotate in mutually opposite directions. The anvil roller 50 cuts the continuum A2 in cooperation with the cutting roller 70 to form the absorber A. The anvil roller 50 transports the separated absorber A to the intermediate transporter 10.

In the present embodiment, the anvil roller 50 receives the continuum A2 at an upper end thereof, cuts the continuum A2 in the vicinity of the receiving position, and subsequently delivers the absorber A to the intermediate transporter 10 at a lower end thereof.

The peripheral speed of the anvil roller 50, i.e. the transport speed of the anvil roller 50, is greater than the speed at which the continuum A2 is delivered to the anvil roller 50, i.e. the transport speed of the continuum A2 to the anvil roller 50. Therefore, the continuum A2 slips upstream in the transport direction from the delivery thereof to the anvil roller 50 to the cutting thereof. This is to space adjacent absorbers A and dispose each absorber A at a position corresponding to a holding pad 40 described later so that the absorber A is appropriately delivered to the holding pad 40.

Figure 8:
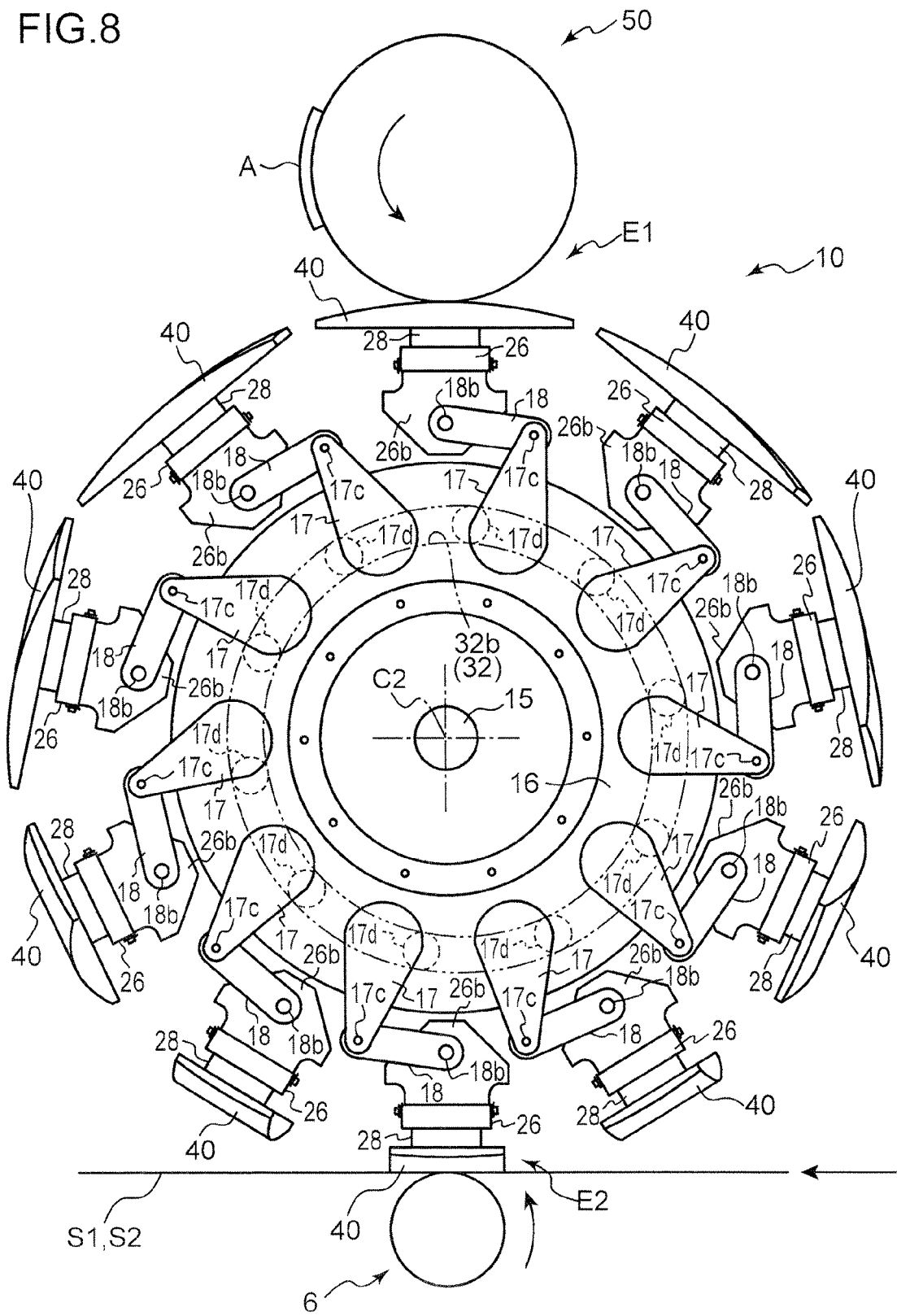
FIG. 8 is a schematic front view of an intermediate transporter.

The intermediate transporter 10 includes, as shown in FIG. 8, a main section 15 rotatable about a second rotational axis C2 extending in parallel to the first rotational axis C1, and a plurality of holding pads 40 attached to the main section 15 in such a way as to revolve about the second rotational axis according to the rotation of the main section 15. The main section 15 and the holding pads 40 rotate and revolve in an opposite direction to the anvil roller 50.

The intermediate transporter 10 receives the absorber A onto an outer surface of the holding pad 40 (radially outer surface of the main section 15) from a circumferential surface of the anvil roller 50 when the holding pad 40 is at a first delivery position (first revolution position) E1 where the holding pad 40 faces the anvil roller 50. Thereafter, the intermediate transporter 10 moves the holding pad 40 to a second delivery position (second revolution position) E2 and delivers the absorber A onto the sheets S1 and S2 from the outer surface of the holding pad 40 at the second delivery position. At the second delivery position E2, the absorber A is pressed against the sheets S1 and S2 to be joined thereto.

Further, the intermediate transporter 10 transports the holding pad 40, together with the absorber A, to the sheets S1 and S2 from the first delivery position E1 to the second delivery position E2 while turning them. Specifically, the holding pad 40 turns about a turning axis perpendicularly intersecting the second rotational axis C2. As mentioned above, in the present embodiment, the holding pad 40 and the absorber A turn through 90 degrees in the course of the movement from the first delivery position E1 to the second delivery position E2.

In the present embodiment, the first delivery position E1 is set at a highest position in the movement of the holding pad 40, and the second delivery position E2 is set at a lowest position in the movement of the holding pad 40. The holding pad 40 and the absorber A turn through 90 degrees while the main section 15 rotates 180 degrees.

(ii) Details of Structure of Anvil Roller

Figure 3:
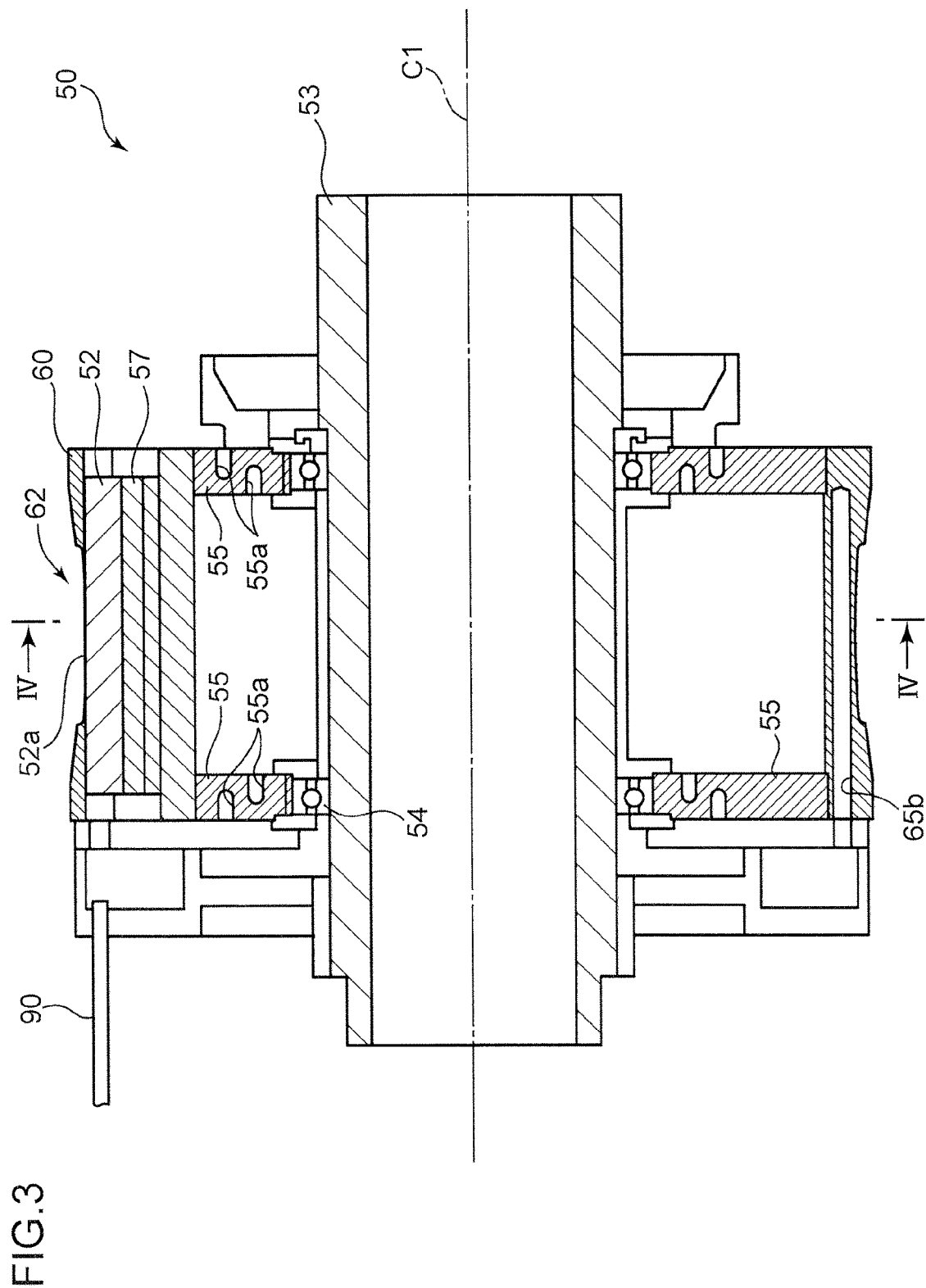
FIG. 3 is a schematic vertical sectional view of an anvil roller.
Figure 4:
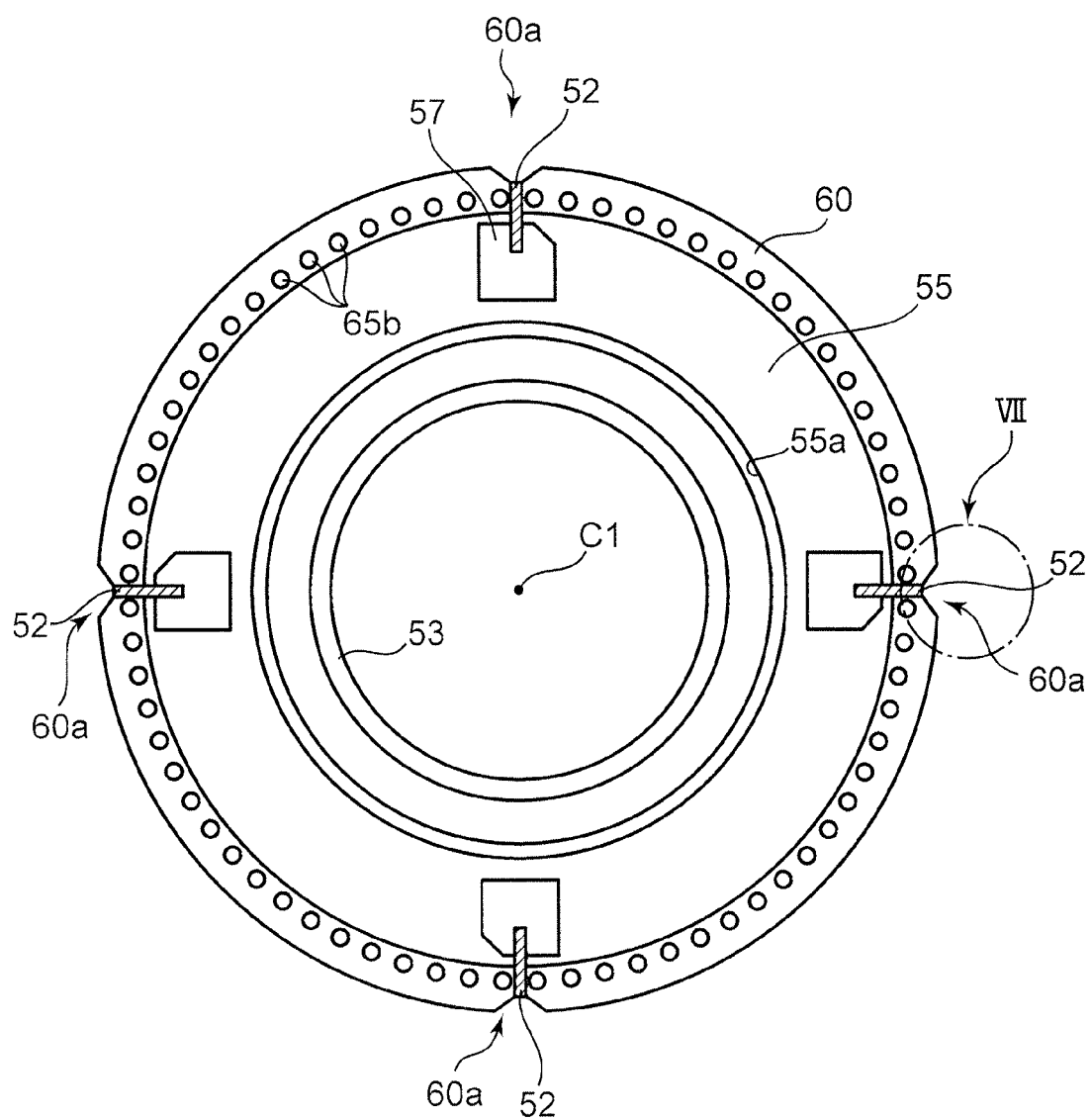
FIG. 4 is a sectional view taken along the line IV-IV shown in FIG. 3.
Figure 5:
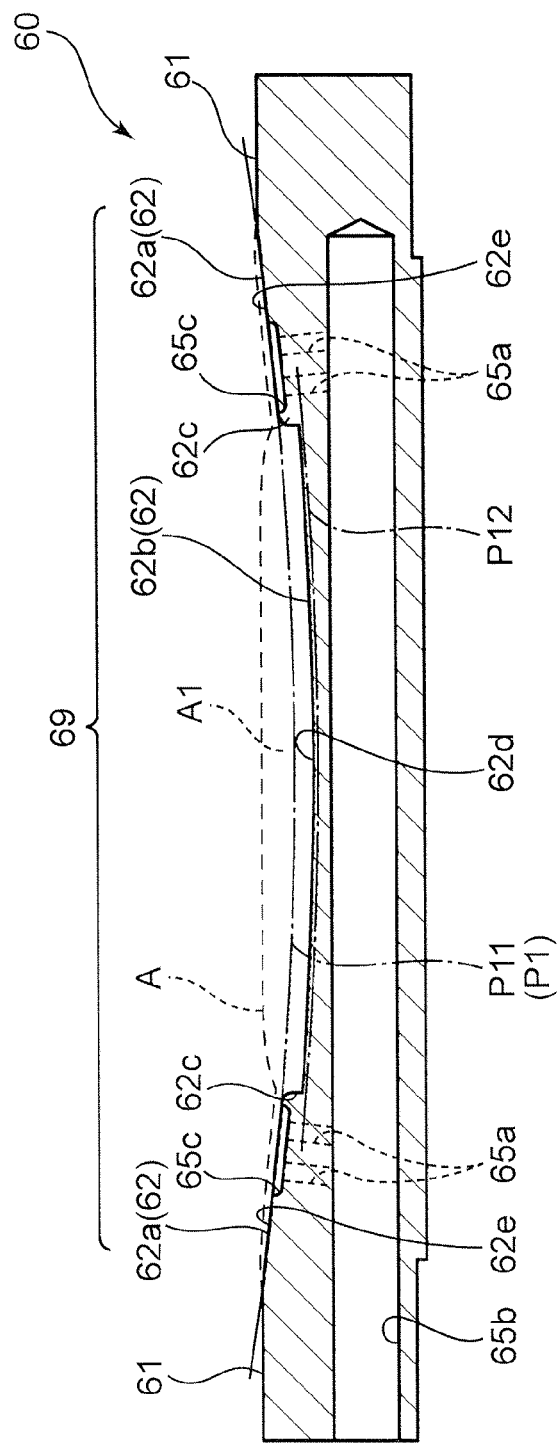
FIG. 5 is an enlarged view of a portion shown in FIG. 3.
Figure 6:
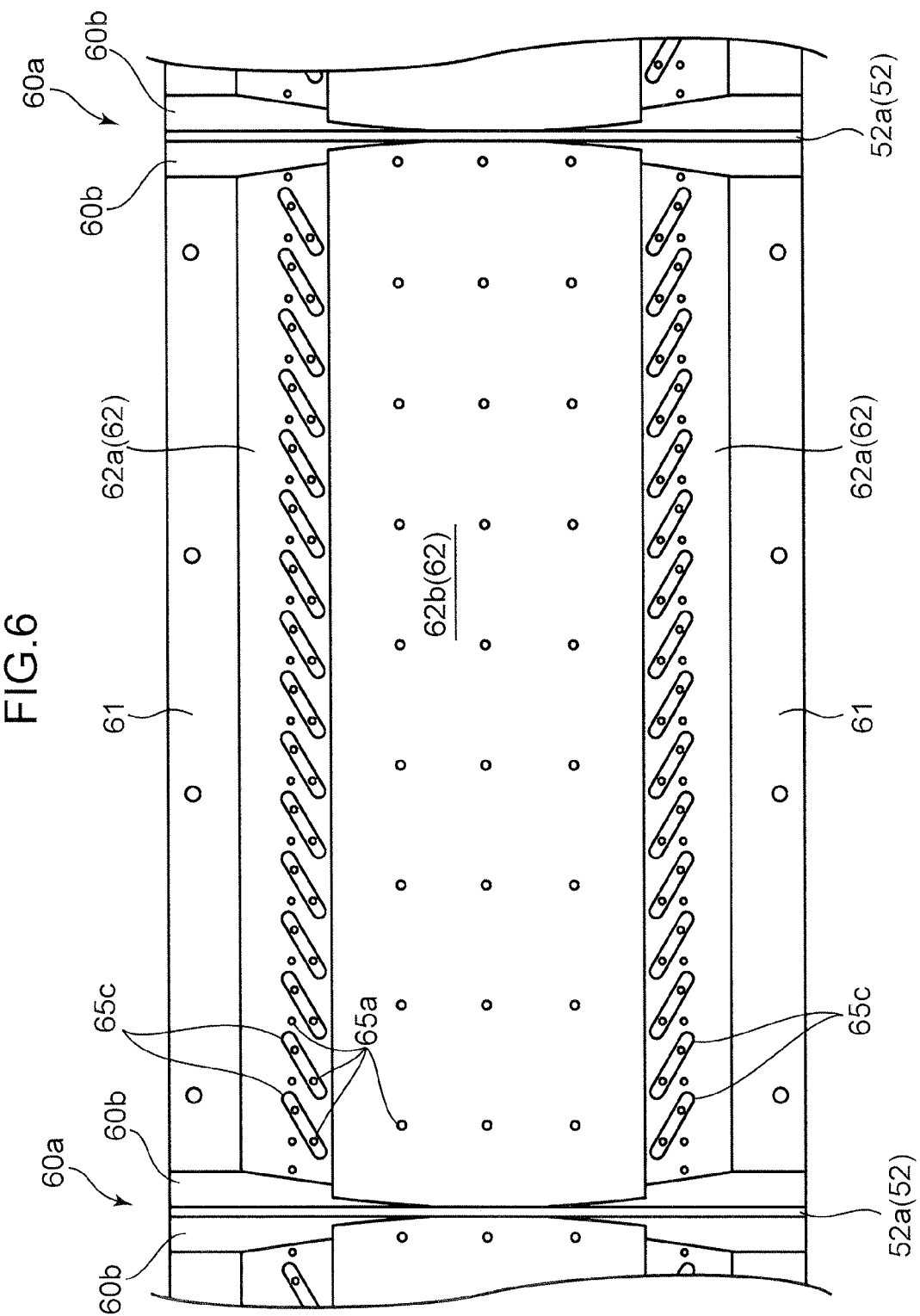
FIG. 6 is an enlarged view of a circumferential surface of the anvil roller.
Figure 7:
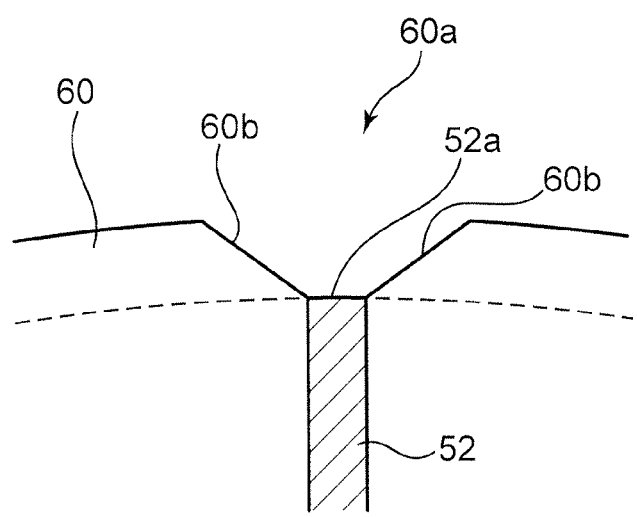
FIG. 7 is an enlarged view of a portion shown in FIG. 4.

Now, the structure of the anvil roller 50 will be described in detail with reference to FIGS. 3 to 7. FIG. 3 is a schematic vertical sectional view of the anvil roller 50. FIG. 4 is a sectional view taken along the line IV-IV shown in FIG. 3. FIG. 5 is an enlarged view of a portion shown in FIG. 3. FIG. 6 is an enlarged view of a portion of the circumferential surface of the anvil roller 50. FIG. 7 is an enlarged view of a portion (denoted by a reference sign VII) shown in FIG. 4.

The anvil roller 50 is attached to a circumferential surface of a stationary drum 53 in the form of a cylinder extending in the front-rear direction in such a way as to be rotatable about the first rotational axis C1 coincident with a central axis of the stationary drum 53. The anvil roller 50 includes a pair of support plates 55, 55, an anvil side holding pad 60, a plurality of anvils (receiving section) 52, a plurality of anvil holders 57. In the present embodiment, the one anvil roller 50 includes four anvils 52 and anvil holders 57 at intervals of 90 degrees, as shown in FIG. 4.

Hereinafter, in the description of the anvil roller 50, a rotational direction of the anvil roller 50 will be simply referred to as "rotational direction", and a radial direction of the anvil roller 50 will be simply referred to as "radial direction".

The support plates 55, 55 are each in the form of a disc-shaped member formed with a circular opening allowing insertion of the stationary drum 53, the opening being formed at a center thereof. The support plates 55, 55 are each attached to the circumferential surface of the stationary drum 53 via a bearing 54 in such a manner as to be rotatable about the first rotational axis C1. The support plates 55 are spaced from each other in the front-rear direction and disposed in parallel to each other.

The anvil 52 meets against the cutting blade 72 and has a plate-like shape. The continuum A2 is cut by being sandwiched and pressed by the cutting blade 72 and the anvil 52.

The anvil holder 57 is in the form of a block for supporting the anvil 52. The anvil holder 52 is secured to the support plates 55, 55, and the anvil 52 is supported on the support plates 55, 55 via the anvil holder 57.

The anvil side holding pad 60 sucks and holds the absorber A on an outer surface (radially outer surface) thereof, and rotates about the first rotational axis C1 together with the support plates 55, 55. The anvil side holding pad 60 is supported by respective circumferential edges of the support plates 55, 55 such that the anvil side holding pad 60 extends across the space between these edges.

The circumferential surface of the anvil roller 50 is constituted by the outer surface of the anvil side holding pad 60 and distal ends (radially outer ends) of the anvils 52, and the anvil side holding pad 60 extends over the substantially entire circumferential edge of each of the support plates 55, 55.

Specifically, as shown in FIGS. 4 and 6, the anvil side holding pad 60 is formed with four cutouts 60a at intervals of 90 degrees. Each anvil 52 is disposed in the cutout 60a such that a distal end 52a of the anvil 52 is exposed, as shown in FIGS. 3 and 4.

The absorber A separated from the continuum A2 is subsequently held on a portion between adjacent cutouts 60a of the anvil side holding pad 60. In the present embodiment, the dimension (widthwise dimension) of the anvil side holding pad 60 in the front-rear direction is greater than the widthwise dimension of the absorber A. Consequently, in the portion of the anvil side holding pad 60 that lies between the adjacent cutouts 60a, the absorber A is held on a region excluding its opposite ends 61, 61 in the front-rear direction. Thus, in the present embodiment, the region of each portion of the anvil side holding pad 60 excluding the opposite ends 61, 61 of the portion in the front-rear direction is set as an anvil side holding region (delivery side holding region) 69 for holding the absorber A , the portion lying between adjacent cutouts 60a.

As shown in FIG. 7, in the present embodiment, the distal end 52a of the anvil 52 has a curved surface extending along the cylindrical surface centered on the first rotational axis C1. This is to reliably bring the cutting blade 72 into contact with the anvil 52. Specifically, in this configuration, even if the position of the cutting blade 72 is deviated, the radial position of the distal end 52a of the anvil 52, i.e. the distance between the distal end 52a of the anvil 52 and the cutting blade 72 would be maintained constant, which therefore would allow the anvil 52 and the cutting blade 72 to appropriately sandwich and press the absorber A.

The anvil side holding pad 60 has oblique sections 60b, 60b on both sides of each anvil 52 in the rotational direction, the oblique section sloping radially inward to the anvil 52.

As shown in FIG. 5, the anvil side holding region 69 is formed with a recess 62 extending radially inward. The recess 62 includes first recesses 62a, 62a, and a second recess 62b.

Specifically, the first recesses 62a, 62a are respectively formed on opposite side portions of the anvil side holding region 69 in the front-rear direction, the first recesses 62a, 62a extending radially inward from opposite outer edges of the anvil side holding region 69 in the front-rear direction respectively toward the center of the anvil side holding region 69 in the front-rear direction. In the present embodiment, the first recesses 62a, 62a formed in the opposite side portions of the anvil side holding region 69 in the front-rear direction each extend over the entirety of the anvil side holding region 69 in the rotational direction.

The first recesses 62a, 62a each have a bottom surface 62e whose intersecting line of a plane passing through the first rotational axis C1 and the second rotational axis C2 extends along a first curve P1 along which a portion of the holding region 41 of the holding pad 40 described later extends, when the first recesses 62a, 62a lie at the first delivery position E1 and face the holding region 41.

Here, in the present embodiment, the first curve P1 is on a sphere having a center point on the second rotational axis C2, as described later. Therefore, the respective bottom surfaces 62e of the first recesses 62a, 62a extend along an arc of a circle centered on a point on the rotational central axis C2 at an intersection of a plane passing through the first rotational axis C1 and the second rotational axis C2 in the above-mentioned state. In other words, the first recesses 62a, 62a extend along an arc P11 of a circle centered on a point lying on the opposite side of the anvil side holding pad 60 from the first rotational axis C1.

In addition, the second recess 62b is formed in a middle portion of the anvil side holding region 69, the second recess 62b extending radially further inward than the first recesses 62a, 62a. In the present embodiment, the second recess 62b is formed in the middle portion of the anvil side holding region 69 in the front-rear direction over the entirety thereof in the rotational direction, the second recess 62b extending over the entire portion between the first recesses 62a, 62a. Specifically, an edge of each of the first recesses 62a, 62a that is closer to the middle portion in the front-rear direction has a rising section 62c extending radially inward, the second recess 62b being defined between these rising sections 62c.

The second recess 62b has a bottom surface 62d that extends along an arc P12 concentric with the arc P11 at an intersection of a plane passing through the first rotational axis C1.

Further, the bottom surface 62d of the second recess 62b is radially flush with the distal end 52a of the anvil 52.

Here, the dimension of the second recess 62b in the front-rear direction is substantially equal to that of the widthwise dimension of the absorbent core A1 that is disposed in the second recess 62b. Therefore, as indicated by the broken line in FIG. 5, the absorber A is held on the anvil side holding pad 60 with the absorbent core A1 lying in the second recess 62b and widthwise outer portions of the absorbent core A1 lying in the first recesses 62a, 62a.

A plurality of anvil side suction holes (delivery side suction holes) 65a are formed in the outer surface of the anvil side holding pad 60, as shown in FIG. 6. Further, as shown in FIGS. 4 and 5, communication holes 65b are formed within the anvil side holding pad 60, the holes 65b being arranged in the circumferential direction and extending in the widthwise (front-rear direction) of the anvil side holding pad 60. The anvil side suction holes 65a respectively communicate with these communication holes 65b connecting with a suction source (not shown) such as a suction pump via a chamber defined axially outside the communication holes 65b and an air pipe 90 (see FIG. 3). When the suction source is operated, the air in the anvil side suction holes 65a is sucked radially inward of the anvil side holding pad 60 via the air pipe 90, the chamber, and the communication holes 65b. In this manner, the air in the anvil side suction holes 65a is sucked so that the internal pressure becomes negative, which allows the absorber A to be sucked on the outer surface of the anvil side holding pad 60.

In the present embodiment, as shown in FIG. 6, anvil side suction holes 65a formed in the first recesses 62a, 62a have a highest opening ratio (the opening area of the anvil side suction hole 65a per unit area) so that the suction force is greater at the first recesses 62a, 62a than the suction force at the second recess 62b. In other words, in the anvil side holding region 69, anvil side suction holes 65a lying in opposite side portions in the front-rear direction where the first recesses 62a, 62a are formed have a greater opening ratio than those lying in the other part. In the present embodiment, the anvil side suction holes 65a lying in the second recess 62b is suppressed to less than 10%, for example, about 1%.

In the present embodiment, anvil side suction holes 65a are uniformly formed over the entirety of the first recesses 62a, 62a in the rotational direction.

Further, the first recesses 62a, 62a are each formed with a plurality of anvil side suction grooves (delivery side suction grooves) 65c having a long-hole shape, the opposite grooves extending obliquely away from each other in the front-rear direction as advancing upstream in the transport direction of the absorber A. The anvil side suction grooves 65c are formed at substantially regular intervals in the rotational direction.

These anvil side suction grooves 65c respectively communicate with the plurality of anvil side suction holes 65a. Specifically, the anvil side suction grooves 65c are formed in the bottom surfaces 62e of the first recesses 62a, 62a, and some of the anvil side suction holes 65a are formed in bottom surfaces of the anvil side suction grooves 65c. In other words, in the present embodiment, some anvil side suction holes 65a are opened in the surfaces of the first recesses 62a, 62a, and the other anvil side suction holes 65a are opened in the bottom surfaces of the anvil side suction grooves 65c in the first recesses 62a, 62a. In the present embodiment, two anvil side suction holes 65a are formed in the bottom of one anvil side suction groove 65c.

Respective front and rear surfaces of the support plates 55, 55 are each formed with heat release grooves 55a, 55a, the groove being formed by depressing the surface. The heat release grooves 55a, 55a are formed in circles in the support plate 55, 55 at radially different positions.

These heat release grooves 55a, 55a are provided to suppress thermal expansion of the support plates 55, 55, in particular, thermal expansion of a portion of the support plates 55, 55 on which the anvil 52 is disposed, to suppress damage of the cutting blade 72.

Specifically, the anvil 52 is disposed on the outer circumferential edge of the support plate 55. Therefore, there is a possibility that thermal expansion of the support plate 55 in the rotation may displace the anvil 52 radially outward, which may quickly damage the cutting blade 72 coming into contact with the anvil 52.

In view of this, in the present embodiment, the heat release grooves 55a, 55a are formed in the support plates 55, 55 so that the support plates 55, 55 each have a great surface area and a long heat transfer path extending from the inner circumferential edge (portion closer to the bearing 54) where heat is produced to the outer circumferential edge. This makes the heat less likely to be transferred. Further, the formation of the heat release grooves 55a, 55a makes thermal expansion having occurred in the bearing 54 side of the support plate 55 less likely to be transferred to the anvil 52 side of the support plate 55. Specifically, even if thermal expansion occurs in the bearing 54 side of the support plate 55, deformation of the heat release grooves 55, 55 absorbs distortion due to the thermal expansion, which reduces the magnitude of deformation transmitted to the anvil 52 side of the support plate 55. Therefore, in the present embodiment, heat is released through the heat release grooves 55a, 55a to suppress thermal expansion of the support plates 55, 55 themselves, and also transmission of the heat and the thermal expansion to the portion near the anvil 52 in the support plate 55. Consequently, displacement of the anvil 52 and damage of the cutting blade 72 are suppressed.

(iii) Intermediate Transporter

Figure 9:
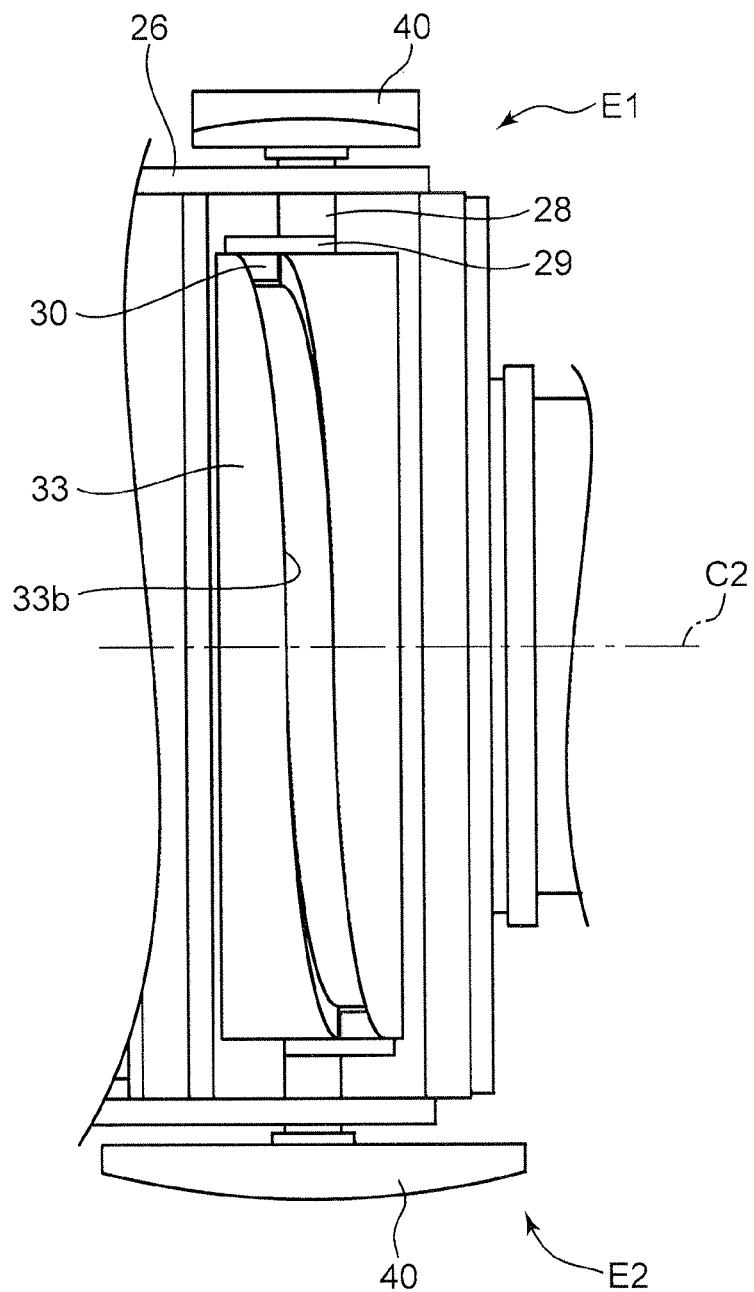
FIG. 9 is a schematic side view of the intermediate transporter.

Now, a specific structure of the intermediate transporter 10 will be described with reference to FIGS. 8 and 9. FIG. 8 is a schematic front view of the intermediate transporter 10. FIG. 9 is a schematic side view of the intermediate transporter 10.

As mentioned above, the intermediate transporter 10 includes the main section 15 and the plurality of holding pads 40. In the present embodiment, the intermediate transporter 10 includes 10 holding pads 40.

The main section 15 is disposed on a predetermined installation surface (not shown) rotatably around the second rotational axis C2 extending in the front-rear direction. Further, a rotation support member 16 integrally rotatable with the main section 15 is secured to the main section 15, and the holding pads 40 are joined to the rotation support member 16.

Hereinafter, in the description of the intermediate transporter 10, a radial direction of the main section 15 will be simply referred to as "radial direction".

The holding pads 40 are arranged on a radially outer side and in a circumferential direction of the rotational support member 16. Each holding pad 40 is supported on a drive base 26 via a turning support 28, the drive base 26 being connected to the rotation support member 16 via an arm 17 and a link lever 18. The turning support 28 is in the form of a cylinder extending in a radial direction.

The intermediate transporter 10 includes a turning cam 33 for turning each holding pad 40 about a turning axis extending in a radial direction, i.e. a direction perpendicularly intersecting the second rotational axis C2, and a transmission cam 32 for changing the peripheral speed of each holding pad 40.

The turning cam 33 is in the form of a cylinder having a central axis coincident with the second rotational axis C2. The turning cam 33 is unrotatably secured to the installation surface of the intermediate transporter 10. As shown in FIG. 9, the turning cam 33 is formed with a turning cam groove 33b formed by depressing a circumferential surface thereof. The turning cam groove 33b includes a portion forming a path along which a position in the front-rear direction changes according to the positional change around the second rotational axis C2.

A cam follower 30 is attached to the turning support 28 via a lever 29, the turning support 28 supporting the holding pad 40. The cam follower 30 engages with the turning cam groove 33b, and is guided along an inner surface of the turning cam groove 33b according to the rotation of the main section 15. When the cam follower 30 is guided along the turning cam groove 33b, the turning support 28 and the holding pad 40 rotate about a central axis of the turning support 28. In other words, the turning axis agrees with the central axis of the turning support 28, and thus the cam follower 30 is guided by the turning cam groove 33b in such a way that the holding pad 40 turns about the turning axis according to the rotation of the main section 15. In this manner, in the present embodiment, the turning cam 33, the lever 29, and the cam follower 30 function as a turning mechanism for turning the holding pad 40. As mentioned above, in the present embodiment, the holding pad 40 turns 90 degrees while the main section 15 rotates 180 degrees.

As shown in FIG. 8, the transmission cam 32 is in the form of a substantially disc-shaped member having the center point of the circle on the second rotational axis C2. The transmission cam 32 is unrotatably secured to the installation surface of the intermediate transporter 10. The transmission cam 32 is formed with a transmission cam groove 32b formed by depressing a front surface thereof. The transmission cam groove 32b has a substantially circular shape having the center point at a position different from the second rotational axis C2.

The transmission cam groove 32b engages with cam followers 17d respectively attached to the arms 17. The cam follower 17d is attached to the arm 17 rotatably about an axis extending in parallel to the second rotational axis C2. When the cam follower 17d is guided along the transmission cam groove 32b according to the rotation of the main section 15, the arm 17 rotates. The rotation of the arm 17 changes the angle between the arm 17 and the link lever 18, which changes the peripheral speed of the drive base 26 secured to the link lever 18 and the holding pad 40.

In the present embodiment, each holding pad 40 revolves about the second rotational axis C2 while being kept at a constant distance from the second rotational axis C2. In other words, each holding pad 40 revolves on a cylindrical surface centered on the second rotational axis C2.

Figure 10:
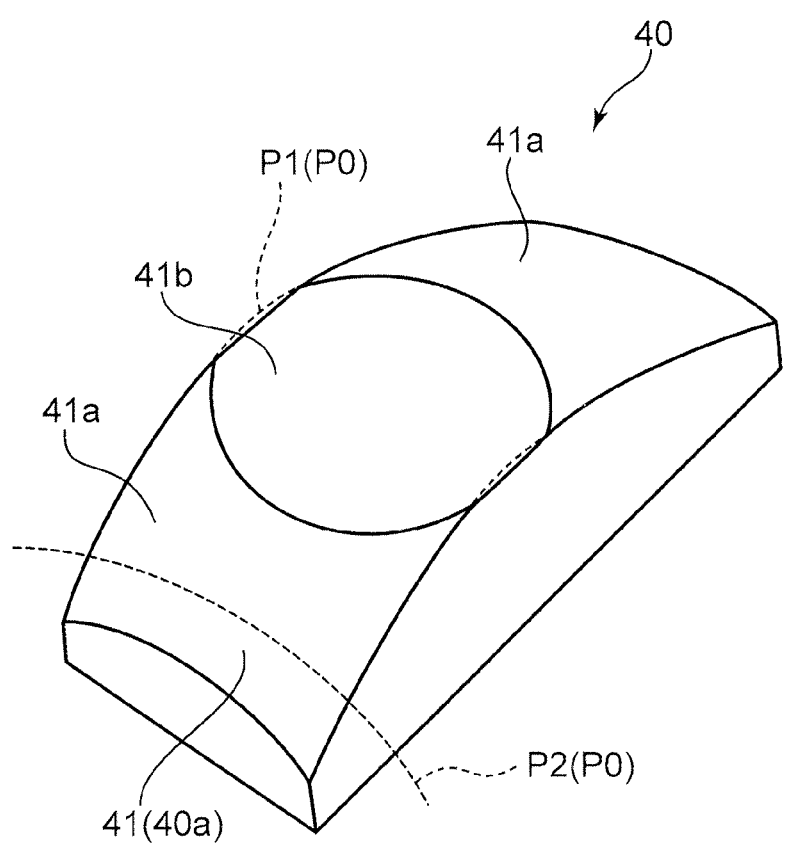
FIG. 10 is an enlarged schematic perspective view of a holding pad.
Figure 11:
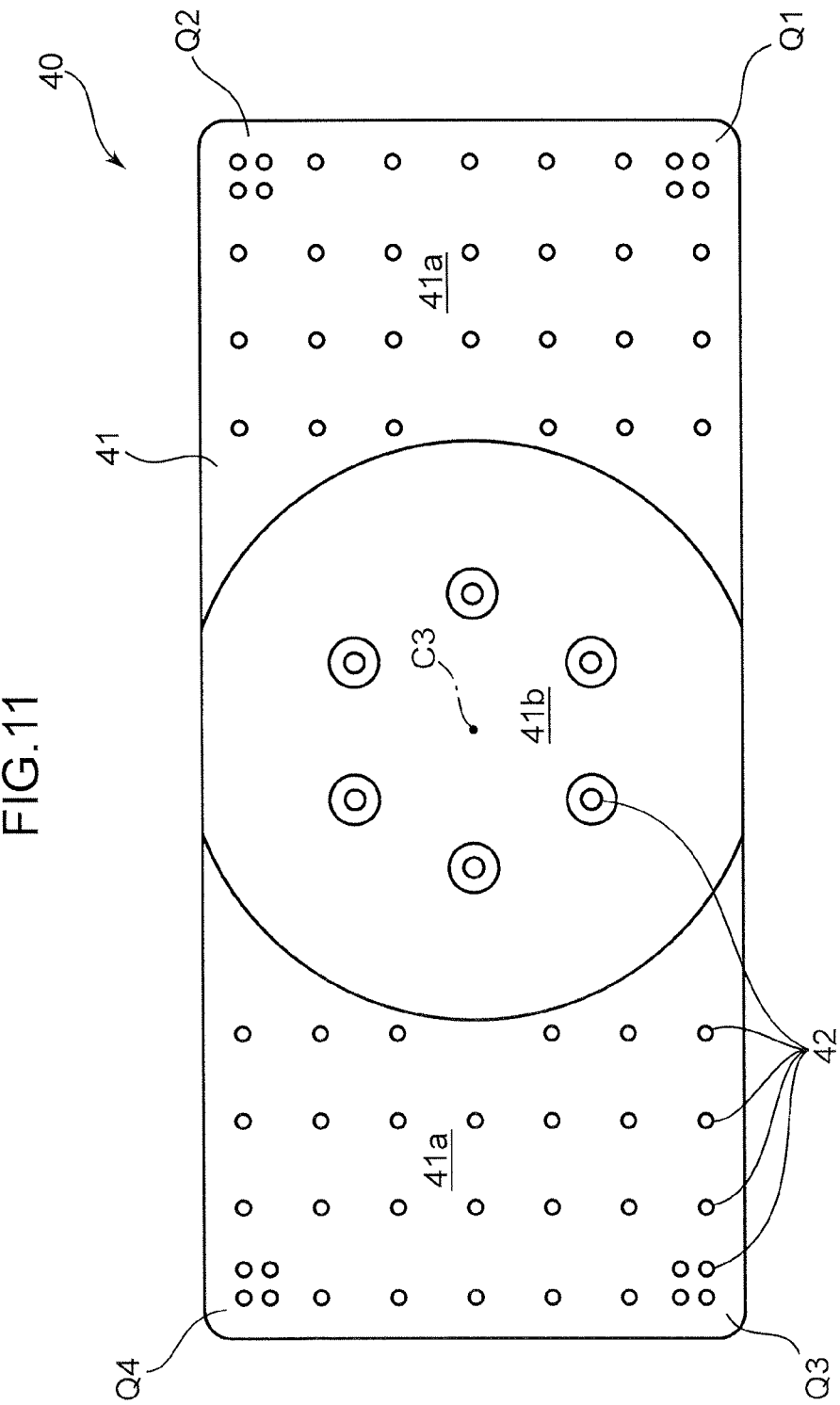
FIG. 11 is a plan view of the holding pad shown in FIG. 10.
Figure 12:
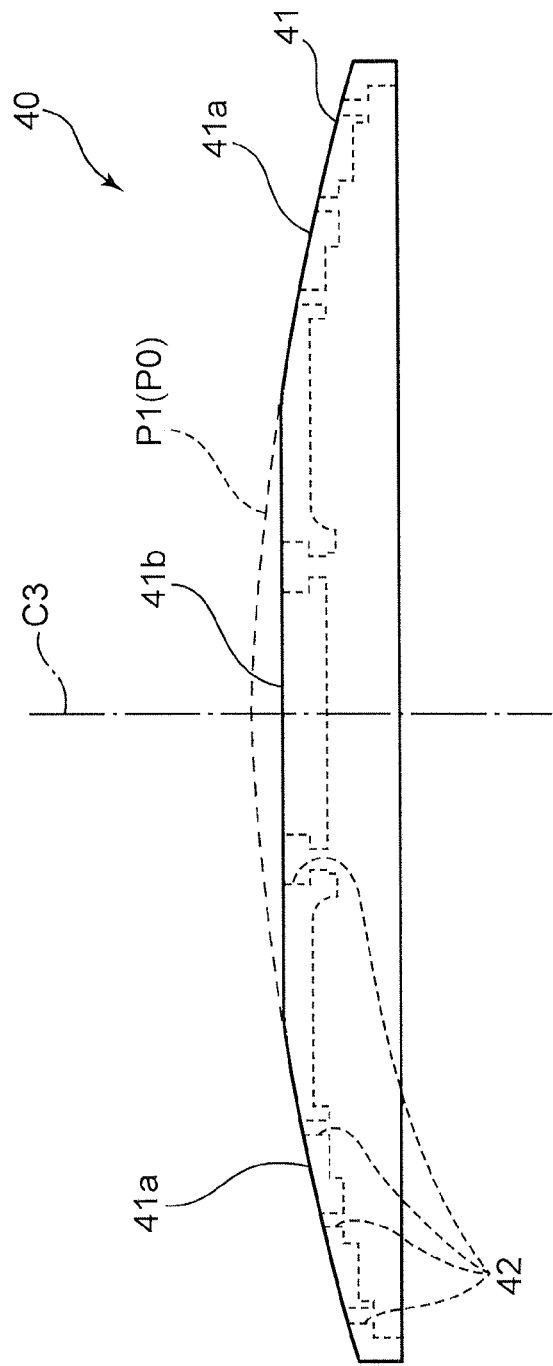
FIG. 12 is a front view of the holding pad shown in FIG. 10.
Figure 13:
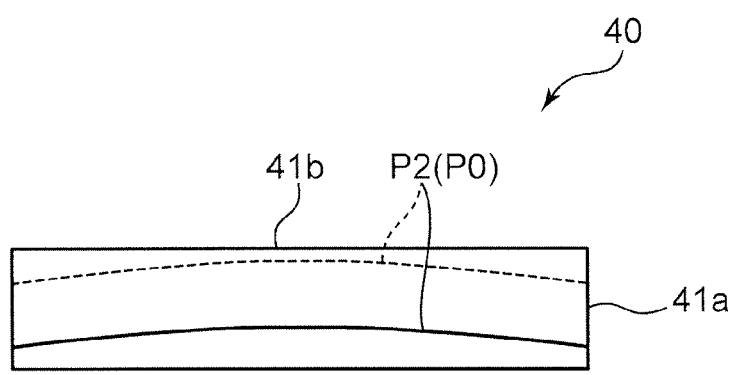
FIG. 13 is a side view of the holding pad shown in FIG. 10.

Now, the structure of the holding pad 40 will be described in detail with reference to FIGS. 10 to 13. FIG. 10 is an enlarged schematic perspective view of the holding pad 40. FIG. 11 is a plan view of the holding pad 40. FIGS. 12 and 13 are front and side views of the holding pad 40, respectively.

The holding pad 40 has an outer surface 40a for holding thereon the absorber A by sucking, the outer surface 40a including the holding region 41 for holding the absorber A. In the present embodiment, the entirety of the outer surface 40a of the holding pad 40 is set as the holding region 41.

In the present embodiment, the holding region 41 has a substantially rectangular shape in plan view in correspondence with the absorber A. Hereinafter, in the description of the holding pad 40, a longitudinal direction of the holding region 41 will be simply referred to as "longitudinal direction", and a width direction of the holding region 41 will be simply referred to as "width direction".

The holding pad 40 has, at the first delivery position E1, a first posture in which the longitudinal direction of the holding region 41 agrees with the rotational direction of the main section 15 and the width direction of the holding region 41 agrees with the front-rear direction. As a result that the holding pad 40 turns 90 degrees in the course of the revolution from the first delivery position E1 to the second delivery position E2, the holding pad 40 has a second posture in which the longitudinal direction of the holding region 41 agrees with the front-rear direction and the width direction of the holding region 41 agrees with the rotational direction of the main section 15.

The holding region 41 includes a first area bearing on at least part of one and at least part of the other of opposite skirt portions in the rotational and revolution direction of the main section 15 and the holding pad 40 (i.e. at least part of one and at least part of the other of opposite skirt portions in the longitudinal direction) when the holding pad 40 is at the first delivery position E1, the first area extending along the first curve P1. Further, the holding region 41 includes a second area bearing on at least part of one side portion and at least part of the other side portion in the rotational direction of the main section 15 and the revolution direction of the holding pad 40 (i.e. at least part of one side portion and at least part of the other side portion in the width direction) when the holding pad 40 is at the second delivery position E2, the second area extending along the second curve P2.

In the present embodiment, the first area is set on the entirety of opposite skirt portions 41a, 41a of the holding region 41 in the longitudinal direction. Further, the second area is set on opposite ends in the longitudinal direction of each of the opposite side portions of the holding region 41 in the width direction, i.e. the four corners of the holding region 41 that are included in the opposite skirt portions 41a, 41a of the holding region 41 in the longitudinal direction.

The first curve P1 is on an arc of a circle centered on the second rotational axis C2 in a view along the second rotational axis C2 when the holding pad 40 is at the first delivery position E1. In other words, as shown in FIG. 12, the opposite skirt portions 41a, 41a of the holding region 41 in the longitudinal direction each extend along an arc at an intersection of a plane perpendicularly intersecting the width direction of the holding pad 40.

Further, the second curve P2 is on an arc of a circle centered on the second rotational axis C2 in a view along the second rotational axis C2 when the holding pad 40 is at the second delivery position E2. In other words, as shown in FIG. 13, the four corners of the holding region 41 each extend along an arc at an intersection of a plane perpendicularly intersecting the longitudinal direction of the holding pad 40.

In the present embodiment, the first curve P1 and the second curve P2 are on the same sphere P0 centered on the intersection of a central axis C3 of the holding pad 40 and the second rotational axis C2, the central axis passing through the center of the holding region 41 and extending in a radial direction. In addition, the entirety of the opposite skirt portions 41a, 41a of the holding region 41 in the longitudinal direction extend along the sphere P0.

On the other hand, a portion of the holding region 41 excluding the first area and the second area lies radially inner than the curves P1 and P2. In the present embodiment, a middle portion 41b of the holding region 41 in the longitudinal direction lies radially inside the sphere P0. Specifically, the middle portion 41b of the holding region 41 in the longitudinal direction is a flat surface perpendicularly intersecting the central axis C3. Further, the middle portion 41b of the holding region 41 in the longitudinal direction has a circular shape in plan view. Further, as shown in FIG. 12, the middle portion 41b of the holding region 41 in the longitudinal direction is a flat surface joining the opposite skirt portions 41a, 41a in the longitudinal direction.

A plurality of holding pad side suction holes 42 are formed in the holding region 41, i.e. the outer surface 40a of the holding pad 40, as shown in FIGS. 11 and 12. These holding pad side suction holes 42 are connected to a suction source (not shown) such as a suction pump, and the suction source is operated to suck the air in the holding pad side suction holes 42 radially inward of the holding pad 40. In this manner, the air in the holding pad side suction holes 42 is sucked so that the internal pressure becomes negative, which allows the absorber A to be sucked on the outer surface 40a of the holding pad 40. It should be noted that the holding pad side suction holes 42 are not shown in FIG. 10.

In the present embodiment, as shown in FIG. 11, holding pad side suction holes 42 formed in the four corners (portions indicated by the reference signs Q1 to Q4 in FIG. 11) have a highest opening ratio, so that the suction force is great at the four corners.

As described above, in the present embodiment, the holding region 41 includes the opposite skirt portions 41a, 41a in the rotational and revolution direction of the main section 15 and the holding pad 40 each of which has at least the opposite ends in the front-rear direction when the holding pad 40 is at the first delivery position E1, the opposite ends extending along the first curve P1 (sphere P0) that is on an arc of a circle centered on the second rotational axis C2 in a view along the second rotational axis C2 in this state. Further, the first recesses 62a, 62a are formed in the opposite side portions of the anvil side holding region 69 of the anvil side holding pad 60 in the front-rear direction, the first recesses each having the bottom surface 62e extending along the first curve P1 (arc P11) at the intersection of the plane passing through the first rotational axis C1 and the second rotational axis C2 when the first recesses 62a, 62a face the holding pad 40.

This makes it possible to more reliably bring the four corners of the absorber A held on the anvil side holding pad 60 into close contact with the four corners of the holding region 41 of the holding pad 40, thereby making it possible to more appropriately deliver the absorber A from the anvil roller 50 onto the holding pad 40.

Furthermore, at least part of one and at least part of the other of the opposite side portions in the rotational and revolution direction of the main section 15 and the holding pad 40 when the holding pad 40 is at the second delivery position E2 extend along the second curve P2 (sphere P0) being on an arc of a circle centered on the second rotational axis C2 in a view along the second rotational axis C2 in this state.

This makes it possible to bring at least part of an upstream side portion and at least part of a downstream side portion of the absorber A in its transport direction into close contact with the sheets S1 and S2 when the absorber A is delivered from the holding pad 40 onto the sheets S1 and S2. Therefore, it is possible to appropriately deliver the absorber A onto the sheets S1 and S2. Specifically, it is possible to prevent displacement of the absorber A which is liable to create wrinkles or the like at the time of the delivery of the absorber A.

In particular, in the present embodiment, the entire upstream end and the entire downstream end in the transport direction of each of the opposite skirt portions 41a, 41a of the holding region 41 in the longitudinal direction extend along the first curve P1 when the holding region 41 is at the first delivery position E1, and the opposite ends in the front-rear direction of the upstream side portion and the opposite ends in the front-rear direction of the downstream side portion of the holding region 41 in the transport direction extend along the second curve P2 when the holding pad 40 is at the second delivery position E2. This makes it possible to more appropriately transport the absorber A while increasing the adhesiveness between the absorber A and the holding pad 40 and the adhesiveness between the absorber A and the sheets S1 and S2.

Further, in the case where an elastic member is attached to the absorber A as in the present embodiment, the absorber A is caused to contract by an elastic force of the elastic member. In view of this, in the present embodiment, it is possible, when the absorber A is delivered, to bring the four corners of the absorber A held on the opposite skirt portions 41a, 41a of the holding region 41 in the longitudinal direction into close contact with the delivery destination portions, as mentioned above. This makes it possible to appropriately join the absorber A onto the sheets S1 and S2 while suppressing the contraction of the absorber A at the time of the delivery of the absorber A.

In this manner, in the present embodiment, it is possible to bring the absorber A into close contact with the holding region 41 of the holding pad 40 and the sheets S1 and S2 while suppressing the creation of wrinkles in the absorber A, thereby making it possible to appropriately transport the absorber A.

Further, the above-described embodiment can provide the following advantageous effects.

The first curve P1 and the second curve P2 lie on the same sphere P0.

Therefore, it is possible to provide the first curve P1 and the second curve P2 in the holding region 41 with a relatively simple structure.

Further, the holding pad side suction holes 42 formed in the opposite ends in the revolution direction of the holding pad 40 of each of the opposite side portions of the holding region 41 in the front-rear direction when the holding pad 40 is at the first delivery position E1, i.e. the holding pad side suction holes 42 formed in the four corners of the holding region 41, have a highest opening ratio, so that the suction force is great at the four corners.

This makes it possible to prevent displacement of the absorber A which is liable to create wrinkles or the like in the absorber A, when the absorber A is transported while being held on the holding pad 40, when the absorber A is delivered from the anvil roller 50 onto the holding pad 40, and the absorber A is delivered from the holding pad 40 onto the sheets S1 and S2. Further, it is possible to suppress the contraction of the absorber A at these times.

Further, the second recess 62b is formed in the middle portion of the anvil side holding region 69, the second recess 62b extending radially further inward than the first recesses 62a, 62a.

This makes it possible to allow the middle portion of the absorber A to recede radially inward of the anvil roller 50 when the absorber A is delivered from the anvil roller 50 onto the holding pad 40. Consequently, it is possible to prevent the four corners of the absorber A from lifting from the outer surface of the holding pad 40 toward the anvil roller 50. As a result, the adhesiveness between the four corners of the absorber A and the holding pad can be increased.

In particular, in the case where the thick absorbent core A1 is disposed in the second recess 62b as in the present embodiment, it is possible to more reliably bring the four corners of the absorber A into close contact with the outer surface of the anvil roller 50 and the holding pad 40 while effectively allowing the absorbent core A1 to recede radially inward of the anvil roller 50.

Further, the bottom surface 62d of the second recess 62b extends along the arc P12 concentric with the arc P11 at the intersection of the plane passing through the first rotational axis C1. This makes it possible to increase the adhesiveness between the portion (absorbent core A1) of the absorber A that lies on the bottom surface 62d of the second recess 62b and its corresponding portion lying in the middle portion in the front-rear direction of each of the opposite skirt portions of the holding pad 40 in the longitudinal direction.

Further, the radially outer end 52a of the anvil 52 is flush with the bottom surface 62d of the second recess 62b in a radial direction the anvil roller 50.

This makes it possible to bring the cutting blade 72 to the position of the bottom surface 62d of the second recess 62b, i.e. the continuum A2 or further inside, in the radial direction of the anvil roller 50. Consequently, it is possible to reliably cut the continuum A2.

Further, the oblique sections 60b, 60b are formed on the both sides of each cutout 60a of the anvil side holding pad 60 in which the anvil 52 is disposed, i.e. on the both sides of each anvil 52 in the rotational direction in the outer surface of the anvil roller 50, the oblique section sloping radially inward of the anvil roller 50 to the anvil 52.

This makes it possible to prevent contact between the cutting blade 72 and the anvil side holding pad 60.

Specifically, the opposite ends 61, 61 in the width direction and the first recesses 62a, 62a of the anvil side holding pad 60 lie radially outside the anvil 52. Therefore, there is a possibility that the cutting blade 72 may come into contact with these portions lying radially outside the anvil 52 on the way toward the anvil 52 or on the way away from the anvil 52. In view of this, in the present embodiment, the oblique sections 60b, 60b are formed to thereby make it possible to prevent contact between the cutting blade 72 and the anvil side holding pad 60.

Further, the first recesses 62a, 62a formed in the opposite side portions of the anvil side holding region 69 in the front-rear direction are formed with the respective anvil side suction grooves 65c having a long-hole shape, the opposite grooves extending obliquely away from each other in the front-rear direction as advancing upstream in the transport direction of the absorber A.

This makes it possible to apply, to the opposite ends of the absorber A in the front-rear direction, forces acting in directions away from each other in the front-rear direction (outward from each other in the front-rear direction) as advancing upstream in the transport direction. Therefore, it is possible to prevent the absorber A from contracting toward the middle portion thereof in the front-rear direction to create wrinkles therein.

Specifically, in the present embodiment, the transport speed of the anvil roller 50 (the peripheral speed of the anvil roller 50) is greater than the speed at which the continuum A2 is supplied to the anvil roller 50. This causes the continuum A2 to slip upstream in the transport direction until the absorber A is cut from the continuum A2. At this time, the opposite ends of the slipping continuum A2 in the front-rear direction are each caused to slip in the longitudinal direction of the anvil side suction grooves 65c and applied with the force acting outward in the front-rear direction as advancing upstream in the transport direction. This makes it possible to prevent the continuum A2, before the cutting thereof, from being displaced or contracting to create wrinkles therein. It should be noted that the opening shape of the anvil side suction groove 65c is not limited to the above-mentioned long-hole shape.

Further, among the anvil side suction holes 65a formed in the anvil side holding region 69, those formed in the opposite ends of the anvil side holding region 69 in the front-rear direction have a greater opening ratio than those formed in the other part, i.e. the middle portion of the anvil side holding region 69 in the front-rear direction.

This makes it possible to have the opposite ends of the absorber A in the front-rear direction be sucked firmly onto the anvil side holding region 69 to be stably held thereon. Besides, because the suction force is small at the middle portion of the absorber A where the absorbent core A1 is disposed and thereby the permeability is low, the absorber A is allowed to easily slip upstream in the transport direction before the continuum A2 is cut.

As described above, in the present embodiment, it is possible to transport and join the absorber A appropriately onto the sheets S1 and S2 while reducing the occurrence of wrinkles and the contraction, by means of the transport device 101 including the anvil roller 50 and the intermediate transporter 10. Therefore, it is possible to produce disposable diapers 1 having a high quality by using the transport device 101 for the production of the disposable diapers 1.

It should be noted that the present invention is not limited to the above-described embodiment, and may adopt the following configurations, for example.

The first area of the holding region 41 that extends along the first curve P1 only has to be at least the opposite ends in the front-rear direction of each of the opposite skirt portions of the holding pad 40 in the revolution direction of the holding pad 40 when the holding pad 40 is at the first delivery position E1. Further, the second area of the holding region 41 that extends along the second curve P2 only has to be at least part of one side portion and at least part of the other side portion in the revolution direction of the holding pad 40 when the holding pad 40 is at the second delivery position E2. The first and second areas are therefore not limited to the portions specified in the above-described embodiment.

Figure 14:
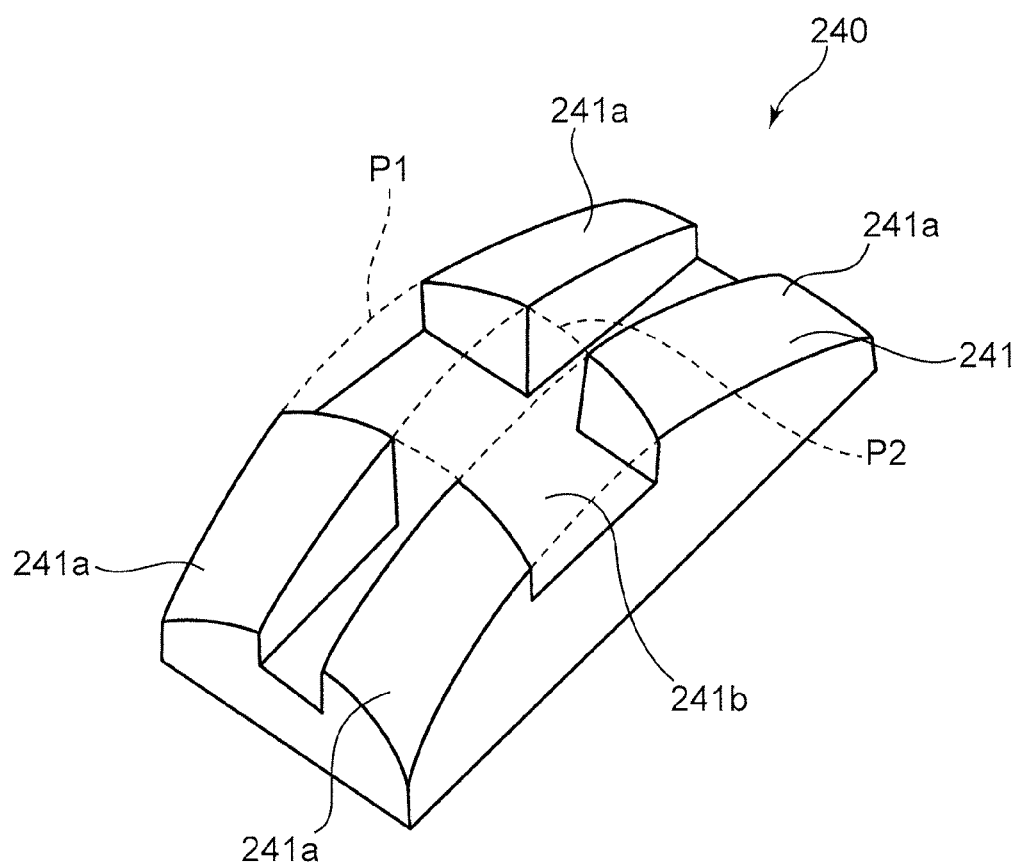
FIG. 14 is a schematic perspective view showing a modified holding pad.

For example, it may be configured such that only the four corners of the holding region each extend along the curves P1 and P2. Specifically, a holding pad shown in FIG. 14 may be used. Specifically, it may be configured such that, in an outer surface 241 of the holding pad 240, only opposite ends 241a in a width direction of each of opposite skirt portions in a longitudinal direction (four corners of the outer surface 241) extend along a curve P2, and the other part 241b lies radially inside the curve P2. In addition, as shown in FIG. 14, in the outer surface 241 of the holding pad 240, the part 241b of each of the opposite skirt portions in the longitudinal direction excluding the opposite ends 241a in the width direction may be recessed radially inward with respect to the opposite ends 241a in the width direction of each of the opposite skirt portions in the longitudinal direction.

Further, the shape of the part of the holding region 41 excluding the portions that extend along the curves P1 and P2 is not limited to the above-described one. For example, such a shape may be adopted that the entire holding region 41 bulges radially outward of the main section 15 with the entire holding region 41 extending along the sphere P0. In this case, when it is configured, as in the above-described embodiment, such that the middle portion 41b of the holding region 41 in the longitudinal direction lies radially inside the sphere P0, i.e. the first curve P1 and the second curve P2, it is possible to prevent the middle portion of the absorber A from being bent along the sphere P0, i.e. each of the curves P1 and P2. when the absorber A is held on the holding region 41. Consequently, it is possible to prevent creation of wrinkles in the absorber A due to the bending. In particular, in the present embodiment, the absorbent core A1 having a great thickness is disposed in the middle portion of the absorber A, and therefore, if such thick middle portion of the absorber A is bent along the sphere P0, i.e. each of the curves P1 and P2, a radially inner portion (portion on the side of the holding pad 40) of the absorber A would contract to create many wrinkles. In view of this, in the present embodiment, it is possible to suppress the bending of the middle portion of the absorber A to thereby effectively prevent the creation of wrinkles.

Further, it may be configured such that only part of the four corners of the holding region extends along the second curve P2. For example, it may be configured such that only one end in the front-rear direction of the one side portion in the revolution direction of the holding pad 40 and the other end in the front-rear direction of the other side portion in the revolution direction of the holding pad 40 when the holding pad 40 is at the second delivery position E2 extend long the second curve P2.

Further, the planar shape of the absorber A and the corresponding holding region 41 of the holding pad 40 are not limited to the above-mentioned rectangular shape. For example, shapes such as a rectangle with curved corners, an oval, a square may be adopted.

For example, in the case where the holding region has an oval shape or the like, only the middle portion in the front-rear direction of each of the opposite side portions in the revolution direction of the holding pad 40 at the second delivery position E2 may be configured to extend along the second curve P2.

Further, it may be configured such that the anvil roller 50 transports the absorber A in such a way that the longitudinal direction of the absorber A agrees with the central axis C1 of the anvil roller 50, and the holding pad 40 resting at the first delivery position E1 is oriented such that the longitudinal direction thereof extends along the rotational central axis C2 and the holding pad 40 resting at the second delivery position E2 is oriented such that the width direction thereof extends along the rotational central axis C2.

Further, the angle of turning of the holding pad 40 in the course of the movement from the first delivery position E1 to the second delivery position E2 is not limited to 90 degrees. For example, the angle may be set to 60 degrees.

Figure 15:
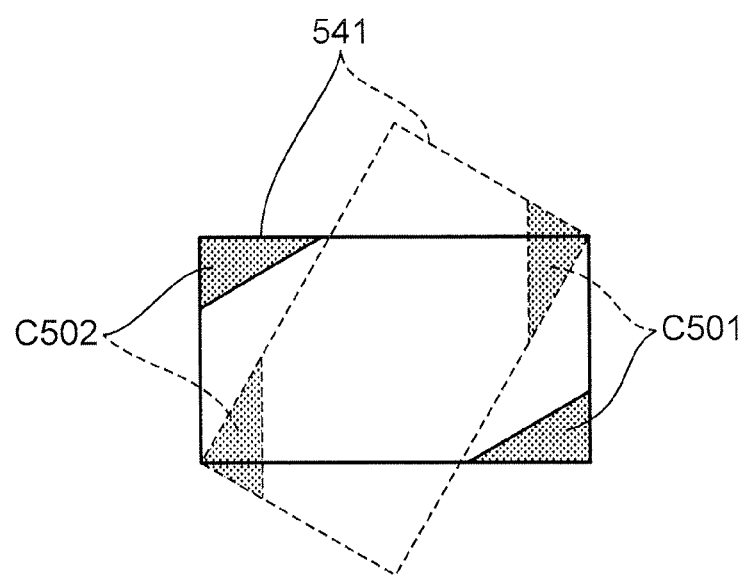
FIG. 15 is a diagram for explaining a structure of a holding region when the holding pad is turned through 60 degrees.

Here, in a case where the angle of turning of the holding pad 40 is set to an angle other than 90 degrees, i.e. a predetermined turning angle between 0 and 180 degrees other than 90 degrees, and a portion extending along the first curve P1 and a portion extending along the second curve P2 overlap, the overlapping portions need to be configured to extend along an arc when viewed from a direction shifted by the turning angle. Therefore, in this case, the first curve P1 and the second curve P2 may be made to lie on the same sphere. For example, in a case where, when the holding pad 40 is viewed from the radially outside of the main section 15, a holding region 541 resting at the first delivery position E1 is in a posture indicated by the solid line and the holding region 541 resting at the second delivery position E2 is in a posture indicated by the dashed line shown in FIG. 15, in order to configure areas including corners C501 and C502 shown in FIG. 15 to extend along the curves P1 and P2, these areas may be configured to extend along a sphere.

Further, the holding pad 40 may be made to lie at different distances from the second rotational axis C2 at the first delivery position E1 and at the second delivery position E2. In this case, the arc of the first curve P1 (the first area) viewed when the holding pad 40 is at the first delivery position E1 and the arc of the second curve P2 (the first area) viewed when the holding pad 40 is at the second delivery position E2 have different radii, i.e. different curvatures. On the other hand, in a case where the holding pad 40 lies at the same distance from the second rotational axis C2 at the first delivery position E1 and the second delivery position E2, the curves P1 and P2 may be made to lie on the same sphere, as mentioned above.

Further, holding pad side suction holes 42 formed in the entirety of the opposite side portions of the holding region 41 in the front-rear direction when the holding pad 40 is at the first delivery position E1 may be made to have a greater opening ratio than the other part.

Further, the first recesses 62a, 62a may be formed only at the opposite ends of the anvil side holding region 69 in the rotational direction of the anvil roller 50.

Further, the second recess 62b may be formed only at the central portion of the anvil side holding region 69 excluding the peripheral portion thereof.

Further, anvil side suction holes 65a formed, in the first recesses 62a, 62a, at the opposite ends of the anvil side holding region 69 in the rotational direction of the anvil roller 50 may be made to have a greater opening ratio than the other part.

Further, the second recess 62b can be omitted. For example, the portion between the first recesses 62a, 62a may be configured to have a cylindrical surface centered on the second rotational axis C2. In this case, it is preferred that the bottom surface 62e of the first recess 62a is flush with the distal end 52a of the anvil 52 in a radial direction to bring the cutting blade 72 to the bottom surface 62e of the first recess 62a, i.e. the continuum A2 or radially further inside, to more reliably cut the continuum A2.

The above-described specific embodiment mainly includes the invention having the following configurations.

In order to achieve the above-mentioned aim, the present invention provides a transport device for transporting an object to a surface of a sheet, comprising: a delivery roller rotatable about a first rotational axis extending in a specific direction for transporting the object while holding the object on a circumferential surface thereof; and an intermediate transporter including a main section rotatable about a second rotational axis extending in parallel to the first rotational axis, and a holding pad mounted on the main section in such a way as to revolve about the second rotational axis according to the rotation of the main section, the holding pad receiving the object onto an outer surface of the holding pad from the circumferential surface of the delivery roller at a first revolution position where the holding pad faces the delivery roller, and delivering the object onto the sheet from the outer surface of the holding pad at a second revolution position, wherein: the outer surface of the holding pad includes a holding region for holding the object; the intermediate transporter includes a turning mechanism for turning the holding pad about a turning axis perpendicularly intersecting the second rotational axis in the course of the movement of the holding pad from the first revolution position to the second revolution position; the holding region includes opposite skirt portions in a revolution direction of the holding pad each of which has at least opposite ends in the specific direction that extend along a first curve when the holding pad is at the first revolution position; the holding region includes a second area bearing on at least part of one side portion and at least part of the other side portion in the revolution direction of the holding pad, the second area extending along a second curve, when the holding pad is at the second revolution position; the first curve is on an arc of a circle centered on the second rotational axis in a view along the second rotational axis when the holding pad is at the first revolution position; the second curve is on an arc of a circle centered on the second rotational axis in a view along the second rotational axis when the holding pad is at the second revolution position; the circumferential surface of the delivery roller includes a delivery side holding region for holding the object; the delivery side holding region includes opposite side portions in the specific direction, each of the side portions having at least opposite ends in a rotational direction of the delivery roller, each end being formed with a first recess extending radially inward of the delivery roller, the first recess having a bottom surface whose intersecting line of a plane passing through the first rotational axis and the second rotational axis extends along the arc of the first curve in a view along the revolution direction of the holding pad, when the delivery side holding region and the holding region of the holding pad face each other.

In the present invention, the holding region includes a second area bearing on at least part of one side portion and at least part of the other side portion in the revolution direction of the holding pad when the holding pad is at the second revolution position, the second area extending along a second curve, i.e. a curve on an arc of a circle centered on the second rotational axis in a view along the second rotational axis when the holding pad is at the second revolution position. Therefore, it is possible to bring a portion of the object held on the holding pad that corresponds to the second area into close contact with the sheet.

Furthermore, the holding region includes at least opposite ends in the specific direction of each of opposite skirt portions in the revolution direction of the holding pad when the holding pad is at the first revolution position, i.e. at least the four corners of the holding region, that extend along a first curve, i.e. a curve on an arc of a circle centered on the second rotational axis in a view along the second rotational axis when the holding pad is at the first revolution position. Further, the delivery side holding region includes at least opposite ends in the rotational direction of the delivery roller of each of opposite side portions in the specific direction, i.e. at least the four corners of the delivery side holding region, that are each formed with a first recess. The first recess has a bottom surface whose intersecting line of a plane passing through the first rotational axis and the second rotational axis extends along the arc of the first curve when the delivery side holding region faces the holding region. Therefore, it is possible, when the object is delivered from the delivery roller onto the holding pad, to bring the four corners of the object held on the delivery holding region into close contact with the four corners of the holding pad.

This makes it possible, when the object is delivered from the delivery roller onto the holding pad, and when the object is delivered from the holding pad onto the sheet, to prevent displacement of the object which is liable to create wrinkles, thereby making it possible to appropriately transport the object.

The turning mechanism is, for example, configured to turn the holding pad through 90 degrees in the course of the movement of the holding pad from the first revolution position to the second revolution position.

It is preferred that the first curve and the second curve be on a sphere having a center point on the second rotational axis.

According to this configuration, it is possible to provide the first area and the second area extending along the first curve and the second curve, respectively, in the holding region relatively easily.

In addition, it is, for example, configured such that the turning mechanism turns the holding pad through a predetermined angle between 0 and 180 degrees other than 90 degrees in the course of the movement of the holding pad from the first revolution position to the second revolution position, that the holding pad is mounted on the main section such that the holding pad lies at the same distance from the second rotational axis at the first revolution position and at the second revolution position, and that the first curve and the second curve are on a sphere having a center point on the second rotational axis.

Also in this configuration, it is possible to provide the first area and the second area extending along the first curve and the second curve, respectively, in the holding region relatively easily.

It is preferred that the delivery roller include a receiving section which is a part of the circumferential surface, and meets against a cutting blade for separating the object from a continuum, and that the receiving section have an outer end in a radial direction of the delivery roller, the outer end being radially flush with the bottom surface of the first recess.

According to this configuration, it is possible to bring the cutting blade to the bottom surface of the first recess, i.e. the object or further inside, in the radial direction so that the object is reliably cut.

It is preferred that the delivery side holding region include a middle portion formed with a second recess extending radially inward of the delivery roller further than the first recess.

According to this configuration, it is possible to allow the middle portion of the object to recede radially inward of the delivery roller when the object is delivered from the delivery roller onto the holding pad. Consequently, it is possible to prevent the four corners of the object from lifting from the outer surface of the holding pad toward the delivery roller. As a result, the adhesiveness between the four corners of the object and the holding pad can be increased.

It is preferred that a bottom surface of the second recess have an arc of a circle having the same axis as the bottom surface of the first recess at an intersection of the plane passing through the first rotational axis and the second rotational axis.

According to this configuration, it is possible, when the object is delivered from the delivery roller onto the holding pad, to place the portion of the object that lies in the second recess along the outer surface of the holding pad, to thereby increase the adhesiveness therebetween.

It is preferred that the delivery roller include a receiving section which is a part of the circumferential surface, and meets against a cutting blade for separating the absorber from a continuum, and that the receiving section have an outer end in a radial direction of the delivery roller, the outer end being radially flush with a bottom surface of the second recess.

According to this configuration, it is possible to bring the cutting blade to the bottom surface of the second recess, i.e. the object or radially further inside, to more reliably cut the absorber while preventing contact between the cutting blade and the delivery roller.

It is preferred that the circumferential surface of the delivery roller include oblique sections on both sides of the receiving section in the rotational direction of the delivery roller, each oblique section sloping radially inward of the delivery roller to the receiving section.

According to this configuration, it is possible to prevent contact between the cutting blade and the delivery roller.

It is preferred that the opposite side portions of the delivery side holding region in the specific direction be each formed with a delivery side suction groove for sucking the object, the opposite delivery side suction grooves extending obliquely away from each other in the specific direction as advancing upstream in a transport direction in which the object is transported by the delivery roller.

According to this configuration, it is possible to apply, to the opposite ends of the object in the specific direction, forces in directions away from each other in the specific direction toward the upstream side in the transport direction. Therefore, it is possible to prevent the object from contracting toward the center thereof in the specific direction to create wrinkles.

It is preferred that the delivery side holding region be formed with a plurality of delivery side suction holes for sucking the object, and that in the opposite side portions of the delivery side holding region in the specific direction, at least delivery side suction holes lying on opposite ends in the rotational direction of the delivery roller have a greater opening ratio than a delivery side suction hole lying in the other part, the opening ratio representing an opening area of the delivery side suction hole per unit area.

According to this configuration, it is possible to have the four corners of the object be stably held on the circumferential surface of the delivery roller.

The present invention further provides a method for producing a disposable wearable article using the transport device configured in the above-mentioned manner, the wearable article including a waist section to be placed around the waist of a wearer and a crotch section to be placed on the crotch of the wearer, the method comprising: a waist sheet transport step of transporting a sheet for forming the waist section in a longitudinal direction thereof; an absorber joining step of transporting an absorber to be placed on a portion corresponding to the crotch section using the transport device and joining the absorber to the sheet to form a joined assembly; a double folding step of folding the joined assembly in half in a direction perpendicularly intersecting the longitudinal direction; a side seal formation step of forming side seals by joining overlapping portions of the sheet that lie on both sides of the absorber in the longitudinal direction; and a cutting step of cutting the sheet in such a way that the side seals remain on the portions on the both sides of the absorber in the longitudinal direction to Corm a disposable wearable article.

According to this method, it is possible to appropriately transport and join the absorber onto the sheet, using the transport device capable of appropriately transporting the object as described above.

Moreover, it is possible to produce the disposable wearable article by folding the joined assembly obtained by joining the absorber and the sheet in half, forming the side seals in the joined assembly, and cutting the waist section sheet.

As a result, it is possible to prevent creation of unexpected wrinkles in the absorber and the sheet, and in turn, in the entire wearable article.

The invention claimed is:

1. A transport device for transporting an object to a surface of a sheet, comprising:
   a delivery roller rotatable about a first rotational axis extending in a specific direction for transporting the object while holding the object on a circumferential surface thereof; and
   an intermediate transporter including a main section rotatable about a second rotational axis extending in parallel to the first rotational axis, and a holding pad mounted on the main section in such a way as to revolve about the second rotational axis according to the rotation of the main section, the holding pad receiving the object onto an outer surface of the holding pad from the circumferential surface of the delivery roller at a first revolution position where the holding pad faces the delivery roller, and delivering the object onto the sheet from the outer surface of the holding pad at a second revolution position, wherein:

the outer surface of the holding pad includes a holding region for holding the object;

the intermediate transporter includes a turning mechanism for turning the holding pad about a turning axis perpendicularly intersecting the second rotational axis in the course of the movement of the holding pad from the first revolution position to the second revolution position;

the holding region includes opposite skirt portions in a revolution direction of the holding pad each of which has at least opposite ends in the specific direction that extend along a first curve when the holding pad is at the first revolution position;

the holding region includes a second area bearing on at least part of one side portion and at least part of the other side portion in the revolution direction of the holding pad, the second area extending along a second curve, when the holding pad is at the second revolution position;

the first curve is on an arc of a circle centered on the second rotational axis in a view along the second rotational axis when the holding pad is at the first revolution position;

the second curve is on an arc of a circle centered on the second rotational axis in a view along the second rotational axis when the holding pad is at the second revolution position;

the circumferential surface of the delivery roller includes a delivery side holding region for holding the object;

the delivery side holding region includes opposite side portions in the specific direction, each of the side portions having at least opposite ends in a rotational direction of the delivery roller, each end being formed with a first recess extending radially inward of the delivery roller, the first recess having a bottom surface whose intersecting line of a plane passing through the first rotational axis and the second rotational axis extends along the arc of the first curve in a view along the revolution direction of the holding pad, when the delivery side holding region and the holding region of the holding pad face each other.

2. The transport device according to claim 1, wherein the turning mechanism turns the holding pad through 90 degrees in the course of the movement of the holding pad from the first revolution position to the second revolution position.

3. The transport device according to claim 2, wherein the first curve and the second curve are on a sphere having a center point on the second rotational axis.

4. The transport device according to claim 1, wherein:
the turning mechanism turns the holding pad through a predetermined angle between 0 and 180 degrees other than 90 degrees in the course of the movement of the holding pad from the first revolution position to the second revolution position;

the holding pad is mounted on the main section such that the holding pad lies at the same distance from the second rotational axis at the first revolution position and at the second revolution position; and the first curve and the second curve are on a sphere having a center point on the second rotational axis.

5. The transport device according to claim 1, wherein
the delivery roller includes a receiving section which is a part of the circumferential surface, and meets against a cutting blade for separating the object from a continuum; and the receiving section has an outer end in a radial direction of the delivery roller, the outer end being radially flush with the bottom surface of the first recess.

6. The transport device according to claim 1, wherein
the delivery side holding region includes a middle portion formed with a second recess extending radially inward of the delivery roller further than the first recess.

7. The transport device according to claim 6, wherein
a bottom surface of the second recess has an arc of a circle having the same axis as the bottom surface of the first recess at an intersection of the plane passing through the first rotational axis and the second rotational axis.

8. The transport device according to claim 6, wherein:
the delivery roller includes a receiving section which is a part of the circumferential surface, and meets against a cutting blade for separating the object from a continuum; and the receiving section has an outer end in a radial direction of the delivery roller, the outer end being radially flush with a bottom surface of the second recess.

9. The transport device according to claim 5, wherein
the circumferential surface of the delivery roller includes oblique sections on both sides of the receiving section in the rotational direction of the delivery roller, each oblique section sloping radially inward of the delivery roller to the receiving section.

10. The transport device according to claim 1, wherein:
the opposite side portions of the delivery side holding region in the specific direction are each formed with a delivery side suction groove for sucking the object, the opposite delivery side suction grooves extending obliquely away from each other in the specific direction as advancing upstream in a transport direction in which the object is transported by the delivery roller.

11. The transport device according to claim 1, wherein:
the delivery side holding region is formed with a plurality of delivery side suction holes for sucking the object;
in the opposite side portions of the delivery side holding region in the specific direction, at least delivery side suction holes lying on opposite ends in the rotational direction of the delivery roller have a greater opening ratio than a delivery side suction hole lying in the other part, the opening ratio representing an opening area of the delivery side suction hole per unit area.

12. A method for producing a disposable wearable article using the transport device according to claim 1, the wearable article including a waist section to be placed around the waist of a wearer and a crotch section to be placed on the crotch of the wearer, the method comprising:

a waist sheet transport step of transporting a sheet for forming the waist section in a longitudinal direction thereof;

an absorber joining step of transporting an absorber to be placed on a portion corresponding to the crotch section using the transport device and joining the absorber to the sheet to form a joined assembly;

a double folding step of folding the joined assembly in half in a direction perpendicularly intersecting the longitudinal direction;

a side seal formation step of forming side seals by joining overlapping portions of the sheet that lie on both sides of the absorber in the longitudinal direction; and a cutting step of cutting the sheet in such a way that the side seals remain on the portions on the both sides of the absorber in the longitudinal direction to form a disposable wearable article.

13. The transport device according to claim 8, wherein the circumferential surface of the delivery roller includes oblique sections on both sides of the receiving section in the rotational direction of the delivery roller, each oblique section sloping radially inward of the delivery roller to the receiving section.

* * * * *